(12) United States Patent
Harlev et al.

(10) Patent No.: US 8,463,368 B2
(45) Date of Patent: Jun. 11, 2013

(54) INTRA-CARDIAC TRACKING SYSTEM

(75) Inventors: Doron Harlev, Brookline, MA (US); Rotem Eldar, Rehovot (IL); Zsolt Badics, Andover, MA (US)

(73) Assignee: Rhythmia Medical, Inc., Burlington, MA (US)

( * ) Notice: Subject to any disclaimer, the term of this patent is extended or adjusted under 35 U.S.C. 154(b) by 0 days.

(21) Appl. No.: 13/466,511

(22) Filed: May 8, 2012

(65) Prior Publication Data

US 2012/0277567 A1 Nov. 1, 2012

Related U.S. Application Data

(62) Division of application No. 12/061,297, filed on Apr. 2, 2008.

(51) Int. Cl.
*A61B 5/04* (2006.01)

(52) U.S. Cl.
USPC .......................................................... 600/509

(58) Field of Classification Search
USPC .................... 600/508–509, 424, 547; 606/34, 606/41
See application file for complete search history.

(56) References Cited

U.S. PATENT DOCUMENTS

| | | | |
|---|---|---|---|
| 4,649,924 A | 3/1987 | Taccardi | |
| 4,674,518 A | 6/1987 | Salo | |
| 4,840,182 A | 6/1989 | Carlson | |
| 4,920,490 A | 4/1990 | Isaacson | |
| 5,156,151 A | 10/1992 | Imran | |
| 5,284,142 A | 2/1994 | Goble et al. | |
| 5,297,549 A | 3/1994 | Beatty et al. | |
| 5,300,068 A | 4/1994 | Rosar et al. | |
| 5,341,807 A | 8/1994 | Nardella | |
| 5,381,333 A | 1/1995 | Isaacson et al. | |
| 5,469,858 A | 11/1995 | Osborne | |
| 5,480,422 A | 1/1996 | Ben-haim | |
| 5,500,011 A | 3/1996 | Desai | |
| 5,553,611 A | 9/1996 | Budd et al. | |
| 5,568,809 A | 10/1996 | Ben-Haim | |

(Continued)

FOREIGN PATENT DOCUMENTS

WO 2008/097767 8/2008

OTHER PUBLICATIONS

Adams, Rolf et al., "Seeded Region Growing", *IEEE transactions on pattern analysis and machine intelligence*, [0162-8328] Adams yr:1994, vol. 16, iss. 6, p. 641, (1994).

(Continued)

*Primary Examiner* — Carl H Layno
*Assistant Examiner* — Paula J Stice
(74) *Attorney, Agent, or Firm* — Fish & Richardson P.C.

(57) ABSTRACT

In general, in one aspect, a method is disclosed for determining information about a position of an object. The method includes: (i) causing current to flow between each of three or more sets of current-injecting electrodes on a first catheter inserted into an organ in a patient's body, the organ having a periphery (ii) in response to current flow caused by each set of current injecting electrodes, measuring an electrical signal at each of one or more measuring electrodes located on one or more additional catheters inserted into the organ in the patient's body and (iii) determining the position of each of one or more of the measuring electrodes on the additional catheters relative to the first catheter based on the measured signals from the one or more measuring electrodes.

77 Claims, 15 Drawing Sheets

U.S. PATENT DOCUMENTS

| | | |
|---|---|---|
| 5,577,502 A | 11/1996 | Darrow et al. |
| 5,588,429 A | 12/1996 | Isaacson et al. |
| 5,662,108 A | 9/1997 | Budd et al. |
| 5,687,737 A | 11/1997 | Branham et al. |
| 5,697,377 A | 12/1997 | Wittkampf |
| 5,704,365 A | 1/1998 | Albrecht et al. |
| 5,722,402 A | 3/1998 | Swanson et al. |
| 5,840,025 A | 11/1998 | Ben-Haim |
| 5,840,031 A | 11/1998 | Crowley |
| 5,848,972 A | 12/1998 | Triedman et al. |
| 5,921,982 A | 7/1999 | Lesh et al. |
| 5,954,665 A | 9/1999 | Ben-Haim |
| 5,971,933 A | 10/1999 | Gopakumaran et al. |
| 5,983,126 A | 11/1999 | Wittkampf |
| 6,050,267 A | 4/2000 | Nardella et al. |
| 6,095,150 A | 8/2000 | Panescu et al. |
| 6,167,296 A | 12/2000 | Shahidi |
| 6,226,542 B1 | 5/2001 | Reisfeld |
| 6,236,886 B1 | 5/2001 | Cherepenin et al. |
| 6,240,307 B1 | 5/2001 | Beatty et al. |
| 6,246,898 B1 | 6/2001 | Vesely et al. |
| 6,254,536 B1 | 7/2001 | DeVito |
| 6,278,894 B1 | 8/2001 | Salo et al. |
| 6,298,257 B1 | 10/2001 | Hall et al. |
| 6,308,093 B1 | 10/2001 | Armoundas et al. |
| 6,314,310 B1 | 11/2001 | Ben-Haim et al. |
| 6,317,619 B1 | 11/2001 | Boernert et al. |
| 6,318,375 B1 | 11/2001 | Plicchi et al. |
| 6,360,123 B1 | 3/2002 | Kimchi et al. |
| 6,368,285 B1 | 4/2002 | Osadchy et al. |
| 6,400,981 B1 | 6/2002 | Govari |
| 6,516,807 B1 | 2/2003 | Panescu et al. |
| 6,547,082 B1 | 4/2003 | Babini |
| 6,556,695 B1 | 4/2003 | Packer et al. |
| 6,574,492 B1 | 6/2003 | Ben-Haim et al. |
| 6,574,498 B1 | 6/2003 | Gilboa |
| 6,593,884 B1 | 7/2003 | Gilboa et al. |
| 6,600,948 B2 | 7/2003 | Ben-Haim et al. |
| 6,603,996 B1 | 8/2003 | Beatty et al. |
| 6,631,290 B1 | 10/2003 | Guck et al. |
| 6,640,119 B1 | 10/2003 | Budd et al. |
| 6,650,927 B1 | 11/2003 | Keidar |
| 6,690,963 B2 | 2/2004 | Ben-haim et al. |
| 6,701,176 B1 | 3/2004 | Halperin et al. |
| 6,728,562 B1 | 4/2004 | Budd et al. |
| 6,773,402 B2 | 8/2004 | Govari et al. |
| 6,807,439 B2 | 10/2004 | Edwards et al. |
| 6,839,588 B1 | 1/2005 | Rudy |
| 6,847,839 B2 | 1/2005 | Ciaccio et al. |
| 6,872,428 B2 | 3/2005 | Yang et al. |
| 6,892,090 B2 | 5/2005 | Verard et al. |
| 6,892,091 B1 | 5/2005 | Ben-Haim et al. |
| 6,939,309 B1 | 9/2005 | Beatty et al. |
| 6,957,101 B2 | 10/2005 | Porath et al. |
| 6,978,168 B2 | 12/2005 | Beatty et al. |
| 6,990,370 B1 | 1/2006 | Beatty et al. |
| 7,016,719 B2 | 3/2006 | Rudy et al. |
| 7,043,292 B2 | 5/2006 | Tarjan et al. |
| 7,263,397 B2 | 8/2007 | Hauck et al. |
| 7,505,810 B2 | 3/2009 | Harlev et al. |
| 7,515,954 B2 | 4/2009 | Harlev et al. |
| 7,729,752 B2 | 6/2010 | Harlev et al. |
| 2002/0151807 A1 | 10/2002 | Goldin |
| 2003/0018251 A1 | 1/2003 | Solomon |
| 2003/0065271 A1 | 4/2003 | Khoury |
| 2003/0076277 A1 | 4/2003 | Muramatsu et al. |
| 2003/0078509 A1* | 4/2003 | Panescu .................. 600/509 |
| 2003/0216630 A1 | 11/2003 | Jersey-Willuhn et al. |
| 2004/0077942 A1 | 4/2004 | Hall et al. |
| 2004/0097806 A1 | 5/2004 | Hunter et al. |
| 2004/0243015 A1 | 12/2004 | Smith et al. |
| 2004/0254437 A1 | 12/2004 | Hauck et al. |
| 2005/0038337 A1 | 2/2005 | Edwards |
| 2005/0054918 A1 | 3/2005 | Sra |
| 2005/0107834 A1 | 5/2005 | Freeman et al. |
| 2005/0154282 A1 | 7/2005 | Li et al. |
| 2006/0085049 A1 | 4/2006 | Cory et al. |
| 2006/0116575 A1 | 6/2006 | Willis |
| 2006/0122526 A1 | 6/2006 | Berenfeld et al. |
| 2006/0173251 A1 | 8/2006 | Govari et al. |
| 2006/0178587 A1 | 8/2006 | Khoury |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0197929 A1 | 8/2007 | Porath et al. |
| 2007/0265539 A1 | 11/2007 | Hastings et al. |
| 2007/0287902 A1 | 12/2007 | Fuimaono et al. |
| 2007/0299351 A1 | 12/2007 | Harlev et al. |
| 2007/0299352 A1 | 12/2007 | Harlev et al. |
| 2008/0190438 A1 | 8/2008 | Harlev et al. |
| 2008/0221566 A1 | 9/2008 | Krishnan |
| 2008/0234588 A1 | 9/2008 | Feldman et al. |
| 2008/0249424 A1 | 10/2008 | Harlev et al. |
| 2009/0171274 A1 | 7/2009 | Harlev et al. |
| 2009/0177072 A1 | 7/2009 | Harlev et al. |
| 2010/0286551 A1 | 11/2010 | Harlev et al. |

OTHER PUBLICATIONS

Arthur, "Clinical Use of Intracardiac Impedance: Current Applications and Future Perspectives", PACE, vol. 24:500-506, Apr. 2001.

Authorized officer, Dorothée Mülhausen, International Preliminary report on Patentability in PCT/US2009/036099, mailed Oct. 14, 2010, 20 pages.

Badics, "Real-Time Reconstruction of Endocardial Potential Maps in Non-Contact Cardiac Mapping", International Journal for computation and Mathematics in Electrical Engineering (COMPEL), vol. 28, No. 4, 2009.

Ben-Haim, Shlorno A. et al., "Nonfluoroscopic, In Vivo Navigation and Mapping Technology", Nat. Med. 2: pp. 1393-1395, (1996).

Besl, Paul J. et al., "A Method for Registration of 3-D Shapes", *IEEE transactions on pattern analysis and machine intelligence*, vol. 14 No. 2, (Feb. 1992).

Blomström-Lundqvist, Carina et al., "Acc/Aha/Esc Guidelines for the Ma Nagement of Patients with Supraventricular Arrhytmias", *J Am Coll Cardiol.*; vol. 42, No. 8, pp. 1493-1531 (Oct. 15, 2003).

Breithardt et al., "AHA Medical/Scientific Statement—Special Report: Standards for Analysis of Ventricular Late Potentials Using High-Resolution or Signal-Averaged Electrocardiography", *Circulation*, 83(4):1481-1488, 1991.

Brooks, Dana et al., "Electrical Imaging of the Heart", *Signal Processing Magazine*, IEEE, vol. 14, Issue: 1 (Jan. 1997).

Caspi et al., "Stem Cell Research: Regenerating the Heart Using Human Embryonic Stem Cells—from Cell to Beside", *IMAJ*, 8:208-214, 2006.

Cheney et al., "Electrical Impedance Tomography", SIAM Review 41:85-101, 1999.

De Groot, Natasja M.S. et al., "Three-Dimensional Catheter Positioning During Radiofrequency Ablation in Patients", *J Cardiovasc Electrophysiol*, vol. 11, pp. 1183-1192, (Nov. 2000).

Donahue et al., "Focal Modification of Electrical Conduction in the Heart by Viral Gene Transfer", *Nature Medicine*, 6(12):1395-1398, 2000.

Dong, Jun et al, "Integrated Electroanatomic Mapping with Three-Dimensional Computed Tomographic Images for Real-Time Guided Ablations", *Circulation*,; 113(2): pp. 186-194, (Jan. 17, 2006).

Durrer, Dirk et al., "Total Excitation of the Isoalted Human Heart", *Circulation*, vol. XLI, (Jun. 1970).

Ector, Joris et al., "Cardiac Three-Dimensional Magnetic Resonance Imaging and Fluoroscopy Merging", *Circulation*. (Dec. 13, 2005).

Friedman, "Catheter, Cryoablation of Cardiac Arrhythmias", *Current Opinion in Cardiology*, 20:48-54, 2005.

Friedman, Paul, "Novel Mapping Techniques for Cardiac Electrophysiology", Heart;87: pp. 575-582 (2002).

Geddes, L.A. et al., "Criteria for the Selection of Materials for Implanted Electrodes", *Annals of Biomedical Engineering*, vol. 31, pp. 879-890 (2003).

Gepstein, Lior et al., "A Novel Method for Nonfluoroscopic Catheter-Based Electroanatomical Mapping of the Heart", *Circulation*; 95, pp. 1611-1622, (1997).

Huang, Yi-Chih et al., "Development of a Third Generation Intraventricular Impedance Imaging (Iii) System Evaluation of Hardware Design", *Engineering in Medicine and Biology Society*, Proceedings of the 19th Annual International Conference of the IEEE, Oct. 30-Nov. 2, 1997 vol. 6, (1997).

International Search Report and the Written Opinion, PCT/US07/70854, Sep. 12, 2008, 15 pages.

International Search Report and he Written Opinion, PCT/US08/52385, Aug. 8, 2008, 11 pages.

Jain et al., "Cell Therapy Attenuated Deleterious Ventricular Remodeling and Improves Cardiac Performance After Myocardial Infarction", *Circulation*, 103:1920-1927, 2001.

Jalife, "Rotors and Spiral Waves in Atrial Fibrillation", *Journal of Cardiovascular Electrophysiology*, 14:776-780, 2003.

Jané, Raimon et al., "Alignment Methods for Averaging of High Resolution Cardiac Signals", *IEEE Transactions in Biomedical Engineering*, vol. 38 No. 6, (Jun. 1991).

Jia, Ping et al., "Electrophysiologic Endocardial Mapping from a Noncontact Nonexpandable Cateter", *J. Cardiovasc Electrophysiol.* vol. 11, pp. 1238-1251, (Nov. 2000).

Kikuchi et al., "Targeted Modification of Atrial Electrophysiology by Homogeneous Transmural Atrial Gene Transfer", *Circulation*, 111:264-270, 2005.

Kistler, Peter M. et al., "Validation of Three-Dimensional Cardiac Image Integration", *J Cardiovasc Electrophysiol*, vol. 17, pp. 341-348, (Apr. 2006).

Lorensen et al. "Marching Cubes: A High Resolution 3D Surface Contruction Algorithm", *Computer Graphics* 21(4):163-169, Jul. 1987.

Mangan, Alan et al., "Partitioning 3D Surface Meshes Using Watershed Segmentation", *IEEE Transactions on Visualization and Computer Graphics*, vol. 05, No. 4, pp. 308-321, (Oct.-Dec. 1999).

Merrill, Daniel R. et al., "Electrical stimulation of excitable tissue: design of efficacious and safe protocols", *Journal of Neuroscience Methods*, vol. 141, pp. 171-198 (2005).

Nademanee et al., "A New Appraoch for Catheter Ablation of Atrial Fibrillation: Mapping of the Electrophysiologic Substrate", *Journal of the American College of Cardiology*, 43(11):2044-2053, 2004.

Notification of Transmittal of the International Search Report and the Written Opinion of the International Searching Authority, or the Declaration, International Application No. PCT/US2009/061277, Apr. 8, 2010, 13 pages.

Pappone, Carlo et al., "Robotic Magnetic Navigation for Atrial Fibrillation Ablation", *Journal of the American College of Cardiology*, vol. 47, No. 7, (2006).

Paragios, Nikos, "A Level Set Approach for Shape-Driven Segmentation and Tracking of the Left Ventricle", *IEEE Transactions on Medical Imaging*, vol. 22, No. 6, (Jun. 2003).

Persson, "Mesh Generation for Implicit Geometrics", *Massachusetts Institute of Technology—Thesis*, Feb. 5, 2006.

Persson, Per-Olof et al., "A Simple Mesh Generator in Matlab", *SIAM Review*, vol. 46 (2), pp. 329-345, (Jun. 1, 2004).

Pham, Dzung et al., "Current Methods in Medical Image Segmentation", *Annu. Rev. Biomed. Eng.*, 02: pp. 315-337, (2000).

Rao, Liyun et al., "Novel Noncontact Catheter System for Endocardial Electrical and Anatomical Imaging", *Annals of Biomedical Engineering*, vol. 32, No. 4, pp. 573-584, (Apr. 2004).

Reddy et al., "Use of a Diode Laser Balloon Ablation Catheter to Generate Circumferential Pulmonary Venous Lesions in an Open-Thoracotomy Caprine Model", *PACE*, 27:52-57, 2004.

Reddy, Vivek et al., "Integration of Cardiac Magnetic Resonance Imaging with Three-Dimensional Electroanatomic Mapping to Guide Left Ventricular Catheter Manipulation", *Journal of the American College of Cardiology*, vol. 44, No. 11, (2004).

Sanders et al., "Spectral Analysis Identifies Sites of High-Frequency Activity Maintaining Atrial Fibrillation in Humans", *Circulation*, 112:789-797, 2005.

Sethian. "Level Set Methods and Fast Marching Methods: Evolving Interfaces in Comptational Geometry, Fluid Mechanics, Computer Vision, and Materials Science". *Department of Mathematics—University of California*, Berkeley, Cambridge University Press, 1999.

Simon et al., "Electroanatomic Mapping of the Right Atrium with a Right Atrial Basket Catheter and Three-Dimensional Intracardiac Echcardiography", *PACE*, 27:318-326, 2004.

Smits et al., "Catheter-Based Intramyocarial Injection of Autologous Skeletal Myoblasts as a Primary Treatment of Ischemic Heart Failure", *Journal of the American College of Cardiology*, 42(12):2063-2069, 2003.

Solomon, Stephen B. et al., "Real-Time Cardiac Catheter Navigation on Three-Dimensional Ct Images", *Journal of Interventional Cardiac Electrophysiology*, 8, pp. 27-36, (2003).

Sra, Jasbir et al, "Registration of 3D Computed Tomographic Images with Interventional Systems: Implications for Catheter Ablation of Atrial Fibrillation", *J Interv Card Electrophysiol*, 16: pp. 141-148, (2006).

Sra, Jasbir et al, "Registration of Three-Dimensional Left Atrial Computed Tomographic Images with Projection Images Obained Using Fluoroscopy", *Circulation*, (Dec. 13, 2005(.

Stevenson, William J. et al., "Radiofrequency Catheter Ablation of Ventricular Tachycardia After Myocardial Infarction", Circulation. ;98, pp. 308-314. (1998).

Taccardi et al., "A New Intracavitary Probe for Detecting the Site of the Origin of Ectopic Ventricular Beats During One Cardiac Cycle", *Circulation*, 75(1):272-281, 1987.

Thal, Sergio G. et al., "Novel Applications in Catheter Ablation", *Journal of Interventional Cardiac Electrophysiology*, 13, pp. 17-21, (2005).

Thiagalingam et al., "Noncontact Mapping of the Left Ventricle: Insights from Validation With Transmural Contact Mapping", *PACE*, 27:570-578, 2004.

USPTO Office Action from U.S. Appl. No. 11/451,898 dated Sep. 25, 2008 (13 pages).

USPTO Office Action from U.S. Appl. No. 11/451,908 dated Sep. 4, 2008 (12 pages).

International Preliminary Report on Patentability, Notification Concerning Transmittal of International Report on Patentability and Written Opinion of the International Search Authority, for Application No. PCT/US2008/052385, dated Aug. 8, 2008, 8 pages.

Voth, "The Inverse Problem of Electrocardiography: Industrial Solutions and Simulations", BEM and NFSI Conference Proceedings, Minneapolis, MN, May 12-15, 2005, pp. 191-194.

Wittkampf, Fred H. et al., "Localisa: New Technique for Real-Time 3-Dimensional Localization of Regular Intracardiac Electrodes", *Circulation*, 99: pp. 1312-1317, (1999).

Yezzi, Anthony et al., "A Geometric Snake Model for Segmentation", *IEEE Transactions on Medical Imaging*, vol. 16, No. 2, (Apr. 1997).

Supplementary European Search Report in European Application No. 09727423.7, mailed May 15, 2012, 5 pages.

International Preliminary Report on Patentability in PCT/US2009/036099, mailed Oct. 14, 2010, 20 pages.

E. J. Haug, K. K. Choi, V. Komkov: Design Sensitivity Analysis of Structural Systems, Matematics in Science and Engineering, vol. 177 (1986).

L. Piegl, W. Tiller: The NURBS Book, 2nd Edition, Springer (1997).

Jané, Raimen et al., "Alignment Methods for Averaging of High Resolution Cardiac Signals", *IEEE Transactions in Biomedical Engineering*, vol. 38 No. 6, (Jun. 1991).

Jia, Ping et al., "Electrophysiologic Endocardial Mapping From a Noncontact Nonexpandable Catheter", *J Cardiovasc Electrophysiol*, vol. 11, pp. 1238-1251, (Nov. 2000).

Kitkuchi et al., "Targeted Modification of Atrial Electrophysiology by Homogeneous Transmural Atrial Gene Transfer", *Circulation*, 111:264-270, 2005.

Kistler, Peter M. et al., "Validation of Three-Dimensional Cardiac Image Integration", *J. Cardiovasc Electrophysiol*, vol. 17, pp. 341-348, (Apr. 2006).

Kuklik et al., "The reconstruction, from a set of points, and analysis of the interior surface of the heart chamber", Physiol. Meas. 25:617-627, 2004.

Kun, Steven et al., "Conductance Volumetric Model of an Eccentrically Positioned Catheter Within a Three-Compartment Ellipsoidal Ventrical", U, IEEE Transactions on, Jun. 1993, vol. 40, Issue: 6.

Laciar, Eric et al., "Improved Alignment Method for Noisy High-Resolution Ecg and Holter Records Using Multiscale Cross-Correlation", *IEEE Transactions on Biomedical Engineering*, vol. 50, No. 3, (Mar. 2003).

Liu et al., "Endocardial Potential mapping from a Noncontact Nonexpandable Catheter: A Feasibility Study", *Annals of Biomedical Engineering*, 26:994-1009, 1998.

Lorensen et al., "Marching Cubes: A High Resolution 3D Surface Construction Algorithm", *Computer Graphics* 21(4):163-169, Jul. 1987.

Makela, Timo et al., "A Review of Cardiac Image Registration Methods", *IEEE Transactions on Medical Imaging*, vol. 21, No. 9, (Sep. 2002).

Malladi, R. et al., "A Geometric Approach to Segmentation and Analysis of 3D Medical Images", *Mathematical Methods in Biomedical Image Analysis*, Proceedings of the Workshop on, Jun. 21-22, 1996, pp. 244-252, (1996).

Mangan, Alan et al., "Partitioning 3D Surface Meshes Using Watershed Segmentation", *IEEE Transactions on Visualization and Computer Graphics*, vol. 05, No. 4, pp. 308-321, (Oct.-Dec., 1999).

Meininger et al., "Initial Experience with a Novel Focused Ultrasound Ablation System for Ring Ablation Outside the Pulmonary Vein", *Journal of Interventional Cardiac Electrophysiology*, 8:141-148, 2003.

Merrill, Daniel R. et al., "Electrical stimulation of exitable tissue: design of efficacious and safe protocols", *Journal of Neuroscience Methods*, vol. 141, pp. 171-198 (2005).

Miller, "Editor's Forum—Application of Registration for Ablation: A Marriage of Technologies", *Journal of Interventional Cardiac Electrophysiology*, 11:87-89, 2004.

Nademanee et al., "A New Approach for Catheter Ablation of Atrial Fibrillation: Mapping of the Electrophysiologic Substrate", *Journal of the American College of Cardiology*, 43(11):2044-2053, 2004.

Noseworthy, Peter A. et al., "The Impact of Respiration on left Atrial and Pulmonary Venous Anatomy: Implications for Image-Guided Intervention", *Heart Rhythm*, vol. 2, No. 11, (Nov. 2005).

Notification of Transmittal of the International Search Report and the Written Opinion of the International Searching Authority, or the Declaration, PCT/US2009/036099, Dated Apr. 28, 2009, 21 pages.

\* cited by examiner

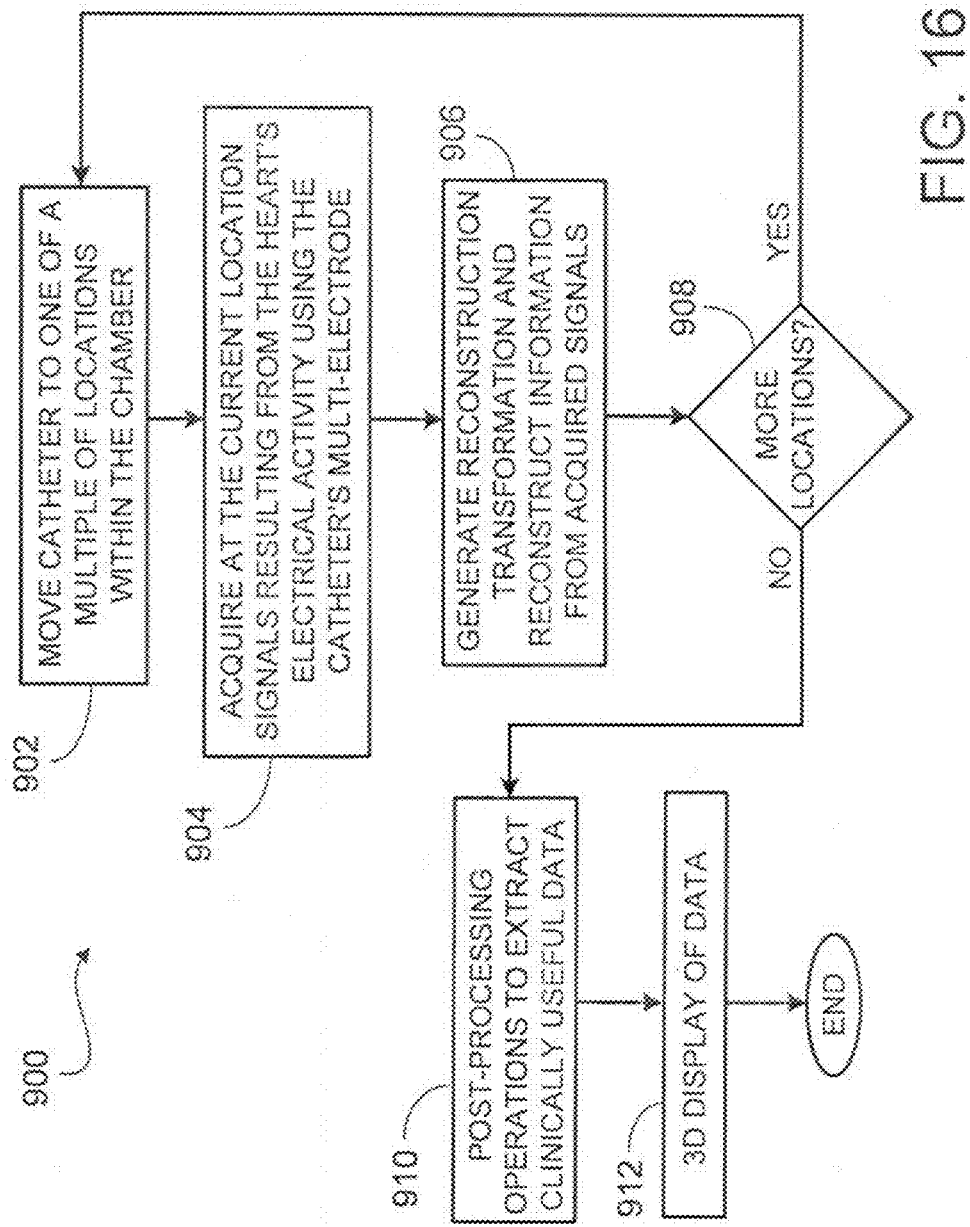

INTRA-CARDIAC TRACKING SYSTEM

CROSS-REFERENCE TO RELATED APPLICATIONS

This is a continuation of U.S. application Ser. No. 12/061,297 filed Apr. 2, 2008. All subject matter set forth in the above referenced application is hereby incorporated by reference into the present application as if fully set forth herein.

TECHNICAL FIELD

This invention relates to determining the position of an object, such as tracking the position of one or more catheters in a patient's heart cavity.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Under some circumstances, the location of the catheter in the heart chamber is determined using a tracking system. Catheter tracking is a core functionality of modern mapping systems that also include software and graphic user interface to project electrical data on 3D renderings of cardiac chambers. Currently there are several tracking systems available, some more useful and commonly used than others. Some systems are based on the use of magnetic or electric fields from external sources to sense and track the location of the catheter. Some are based on the use of magnetic or electric fields sources mounted on the tracked catheters.

SUMMARY

In general, in one aspect, a method is disclosed for tracking a multi-electrode array (MEA) catheter, as well as additional electrodes mounted on other catheters, within and relative to the surface of the organ (e.g., the surface of the cardiac cavity, including any number of chambers within this cavity and the blood vessels surrounding it).

In another aspect, an MEA catheter can include both potential measuring electrodes (PME) and current injecting electrodes (CIE) in known positions relative to one another. Due to the known positions of both the PME and CIE electrodes on the MEA catheter, voltage measurements acquired by the PME can be used to model inhomogeneity in the organ. Using the modeled inhomogeneity, other electrodes can be tracked relative to the MEA catheter without requiring the use of a pre-acquired image.

In general, in some aspects, a method includes tracking a multi-electrode array (MEA) catheter, as well as additional electrodes mounted on other catheters, within and relative to the cardiac cavity. Electrodes can be mounted on one or multiple catheters and by tracking these electrodes the location of such catheters can be determined and the catheters can be tracked. In some aspects, the tracking includes generating a multitude of electrical fields on the MEA catheter, using measurements of these generated fields on the MEA catheter to provide a conductivity calibration and a correction for inhomogeneity in the medium, and using measurements of the same fields on electrodes mounted on other catheters to locate the catheters relative to the MEA catheter.

In general, in one aspect, secured electrodes that are located at fixed, known locations within the organ are used to track other moving catheters relative to the surface of the organ. For example, the electrodes can be secured within the heart and other catheters (e.g., an ablation catheter) can be tracked relative to the surface of the heart. In some aspects, at least three secured electrodes are used to correct a location of another catheter based on a movement of the organ (e.g., a translation of the organ, a rotation of the organ, a movement caused by respiration, and/or a movement caused by movement of the patient). In some aspects, the location of a catheter is tracked relative to the surface of the organ by tracking the location of the MEA catheter in relation to both the secured electrodes and the catheter and performing a calculation to determine the location of the catheter relative to the surface of the heart (e.g., relative to the location of the secured electrodes).

In general, in one aspect, a method is disclosed for determining information about a position of an object. The method includes: (i) causing current to flow between each of three or more sets of current-injecting electrodes on a first catheter inserted into an organ in a patient's body, the organ having a periphery (ii) in response to current flow caused by each set of current injecting electrodes, measuring an electrical signal at each of one or more measuring electrodes located on one or more additional catheters inserted into the organ in the patient's body and (iii) determining the position of each of one or more of the measuring electrodes on the additional catheters relative to the first catheter based on the measured signals from the one or more measuring electrodes.

Embodiments of the method may include any of the following features.

The method can further include measuring electric signals at each of multiple measuring electrodes on the first catheter in response to current flow caused by each set of current injecting electrodes. The determination of the relative position between the first catheter and each of the one or more of the measuring electrodes on the one or more additional catheters can be based on the measured signals from the measuring electrodes on the first catheter and the one or more additional catheters.

The determination can associate each measured signal with a homogeneous component that depends on the relative position of each signal measuring electrode with respect to each set of current injecting electrodes and an inhomogeneous component associated with the periphery of the organ. The periphery of the organ can include various objects surrounding the homogeneous blood medium. In the example of the heart, the periphery of the heart can include the walls of the heart, the lungs surrounding the heart, etc. The inhomogeneous component can be modeled as a variation in electric potential along a surface enclosing at least the first catheter that depends on the relative positions between the current injecting electrodes and the signal measuring electrodes. The homogeneous component can additionally depend on an estimate for conductivity inside the organ. The determination can account for a change in conductivity at the organ's periphery. For example, if the organ comprises the patient's heart, the determination can account for a change in conductivity at the cardiac chamber periphery.

The determination can associate each measured signal with a homogeneous component and an inhomogeneous component associated with the organ's periphery.

The first catheter can include more than 32 measuring electrodes.

The determination can be based on predetermined information about the relative positions of the electrodes on the first catheter.

The determination can use an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter and the change in conductivity at the organ's periphery.

The determination can be an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter and the estimate for conductivity inside the organ.

The determination can be an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter, the change in conductivity at the organ's periphery and the estimate for conductivity inside the organ.

The method can also include using the multiple signal measuring electrodes on the first catheter to measure electrical activity caused by the patient's heart (e.g., a cardiac signal).

The method can also include securing at least three electrodes to be used for reference to fixed locations within the organ. The electrodes used for reference can include measuring electrodes. The method can also include determining the position of each of the electrodes used for reference relative to the first catheter. The at least three electrodes used for reference can be on a single catheter or on multiple catheters.

The method can also include using the determined position of each of the reference electrodes relative to the first catheter to determine a location of each of the one or more electrodes on the one of more additional catheters relative to a surface of the organ. The method can also include displaying the position of the one or more additional catheters relative to the surface of the organ.

The method can also include using the determined position of each of the reference electrodes relative to the first catheter to determine a location of the first catheter relative to the surface of the organ. The method can also include displaying the position of the first catheter relative to the surface of the organ.

The method can also include determining a position of each of the reference electrodes relative to the first catheter and determining a location of each of the one or more electrodes on the one or more additional catheters relative to the surface of the organ. Determining a location of each of the one or more electrodes on the one or more additional catheters relative to the surface of the organ can include correcting a location of the one or more additional catheters based on a movement of the organ. The movement of the organ can include one or more of a translation of the organ, a rotation of the organ, a movement caused by respiration, and/or a movement caused by movement of the patient.

Determining a location of each of the one or more electrodes on the second catheter relative to the surface of the organ can include correcting a location of each of the one or more electrodes on the second catheter based on a movement of the first catheter.

The method can also include using the reference electrodes to generate a fixed coordinate system relative to a surface of the organ.

The method can also include determining the position of each of the one or more measuring electrodes on the second catheter relative to the surface of the organ.

The method can also include determining the position of each of the one or more the measuring electrodes on the second catheter relative to the surface of the organ by solving a minimization between the known locations of the reference electrodes relative to the organ and a determined position of each of the reference electrodes relative to the first catheter.

The method can also include moving the first catheter within the organ relative to the reference electrodes.

The method can also include tracking the position of the first catheter relative to the surface of the organ based on the measured signals on the first catheter and the fixed location of the reference electrodes.

The method can also include using multiple signal measuring electrodes on the first catheter and the one or more electrodes on the one or more additional catheters to measure cardiac signals.

The method can also include using the same one or more measuring electrodes on the one or more additional catheters to measure the electrical signals to determine the position of the one or more electrodes and to measure cardiac signals. The method can also include using one or more electrodes on the one or more additional catheters for delivering ablation energy for ablating tissue of the organ.

The method can also include moving one or more of the additional catheters inside the organ and tracking the position of each of one or more measuring electrodes relative to the surface of the organ based on signals measured by the one or more measuring electrodes in response to current flow caused by each set of current injecting electrodes on the first catheter and the tracked position of the first catheter relative to the surface of the organ.

The method can also include using a catheter to ablate selected regions of the cardiac chamber based on the measured electrical activity and a tracked position of an electrode on the catheter used to ablate the selected regions.

The method can also include moving a catheter that includes an ablation electrode inside the organ and tracking the position of the ablation electrode on that catheter relative to the surface of the organ based on signals measured by the ablation electrode in response to current flow caused by each set of current injecting electrodes on the first catheter. The method can also include using the ablation electrode on the catheter to ablate selected regions of a cardiac chamber.

The one or more additional catheters can be at least two additional catheters, at least three additional catheters, at least four additional catheters, or at least five additional catheters.

Measuring the electrical signal at each of the one or more measuring electrodes on the one or more additional catheters can include simultaneously measuring the electrical signal at each the one or more measuring electrodes on the one or more additional catheters.

In some embodiments, the three or more sets of current-injecting electrodes on the first catheter can include three or more pairs of current-injecting electrodes configured to generate a dipole potential. In some alternative embodiments, the three or more sets of current-injecting electrodes on a first catheter can include three or more sets of current-injecting electrodes configured to generate a quadrupole potential.

The determination can include an optimization technique that minimizes collective differences between each of the measured signals and an estimate for each of the respective measured signals as a function of the relative position between each of the one or more measuring electrodes on the one or more additional catheters and the sets of current-injecting electrodes on the first catheter.

Causing the current to flow between each of the three or more sets of current-injecting electrodes on the first catheter can include modulating the current caused to flow between each of the three or more sets of current-injecting electrodes in one or more of time and frequency.

Determining the position of each of the one or more measuring electrodes on the one or more additional catheters relative to the first catheter based on the measured signals from the one or more electrodes can include distinguishing the current from a particular one of the three or more sets of current-injecting electrodes from other electrical signals. The other electrical signals can include currents from other ones of the three or more sets of current injecting electrodes and/or cardiac signals.

The current can be caused to flow at a frequency outside the frequency range of the patient's cardiac activity. Determining the position of each of the one or more measuring electrodes on the second catheter relative to the first catheter based on the measured signals from the one or more electrodes can include distinguishing cardiac signals from signals responsive to the injected current.

Distinguishing the cardiac signals from those responsive to the injected current can include using a spread spectrum technique.

The determination of the relative position between the first catheter and the one or more electrodes on the one or more additional catheters can be repeated multiple times during the patient's cardiac cycle.

The first catheter can include three or more pairs of current-injecting electrodes. Three of the current injecting electrode sets can define substantially orthogonal axes.

Causing current to flow between each of three or more sets of current injecting electrodes can include sequentially causing current to flow between each of three or more sets of current injecting electrodes.

Causing current to flow between each of three or more sets of current injecting electrodes can include concurrently causing current to flow between multiple sets of the three or more sets of current injecting electrodes and the frequency of the current differs between the sets of current injecting electrodes.

Causing current to flow between each of three or more sets of current injecting electrodes can include modulating each current with information for coding division of the currents from the three or more sets of current injecting electrodes.

Causing current to flow between each of three or more sets of current injecting electrodes can include causing current to flow between each of three or more pairs of current injecting electrodes.

The organ in the patient's body can be the patient's heart, liver, lungs, and/or other organs in the patient's body.

The method can also include using the determined position of each of the one or more electrodes on the one or more additional catheters to determine a position of the one or more additional catheters or portion of one or more of the catheters.

The method can also include using the determined position of each of the one or more electrodes on the one or more additional catheters to determine a position of a portion of a catheter used for ablation.

The method can also include displaying the position of the one or more additional catheters relative to the surface of the organ.

The determination of the position of each of the one or more measuring electrodes on the one or more additional catheters relative to the first catheter can account for a change in conductivity at the organ's periphery. For example, if the organ is the patient's heart, the determination can account for a change in conductivity at a periphery of the cardiac chamber.

The determination can associate each measured signal with a homogeneous component and an inhomogeneous component associated with the organ's periphery. The inhomogeneous component can be modeled as a variation in electric potential along a surface enclosing the first and second catheters that depends on the relative positions between the current injecting electrodes and each of the one or more measuring electrodes. The inhomogeneous component can additionally depend on a regularization parameter. The homogeneous component can correspond to a dipole potential in a medium with a homogeneous conductivity or can correspond to a quadrupole potential in a medium with a homogeneous conductivity. The homogeneous component can depend on the relative position of each signal measuring electrode with respect to each set of current injecting electrodes. The homogeneous component can additionally depend on an estimate for conductivity inside the organ.

The determination can include an optimization technique that minimizes collective differences between each of the measured signals and an estimate for each of the respective measured signals as a function of the relative position between the one or more measuring electrodes on the one or more additional catheters and the first catheter and the estimated conductivity.

In general, in another aspect, a system is disclosed that includes (i) a first catheter configured for insertion into an organ in a patient's body and that includes three or more sets of current injecting electrodes, (ii) one or more additional catheters configured for insertion into the organ in the patient's body and including one or more measuring electrodes (iii) an electronic control system coupled to the first catheter and the one or more additional catheters and configured to cause current to flow between each set of current-injecting electrodes and measure an electrical signal in response to the current flow caused by each set of current injecting electrodes at each of the measuring electrodes on the one or more additional catheters and (iv) a processing system coupled to the electronic system and configured to determine the position of the each of one or more of the one or more current measuring electrodes relative to the first catheter based on the measured signals from the one or more measuring electrodes.

The information about cardiac electrical activity (e.g., cardiac signals) can be based on the measured electrical signals, the spatial information about the heart cavity, and the determined relative position of the catheter. The electronic processor can be further configured to display the information about the cardiac signals on a representation of the patient's heart. The system can further include an ablation catheter for treating a patient's heart condition based on the displayed information about the cardiac signals.

Embodiments of the system may also include devices, software, components, and/or systems to perform any features described above in connection with the first method and/or described below in connection with the second method.

In general, in another aspect, a method includes: (i) determining locations of multiple tracked elements within an organ, the organ having a periphery, (ii) securing at least three of the tracked elements to fixed locations within the organ, (iii) determining the location of one or more other tracked elements relative to the at least three tracked elements secured to the fixed locations within the organ, and (iv) using the locations of the at least three tracked elements secured to the fixed locations within the organ to determine the locations of the one or more other tracked elements relative to the surface of the organ.

Embodiments of the method may include any of the following features.

The tracked elements can be electrodes, catheters, and/or sensors of a tracking system.

The secured tracked elements can be mounted on a single catheter or mounted on separate catheters.

The determination of the locations of the one or more other tracked elements relative to a surface of the organ can account for movement of the organ. The movement of the organ can include a translation of the organ, a rotation of the organ, a movement caused by respiration, and/or a movement caused by movement of the patient.

Embodiments of the method may also include any features described above in connection with the first method.

In some aspects, a system includes multiple tracked elements configured for insertion into an organ in a patient's body at least three of which are configured to be secured to fixed locations within the organ. The system also includes an electronic control system coupled to the tracked elements. The system also includes a processing system coupled to the electronic system and configured to determine locations of the multiple tracked elements within the organ, determine the location of one or more other tracked elements relative to the at least three tracked elements secured to the fixed locations within the organ, and use the locations of the at least three tracked elements secured to the fixed locations within the organ to determine the locations of the one or more other tracked elements relative to the surface of the organ.

Embodiments of the system may include any of the following features.

The tracked elements can be electrodes, catheters, and/or sensors of a tracking system.

The secured tracked elements can be mounted on a single catheter or mounted on separate catheters.

Embodiments of the method may also include any features described herein in connection with the various methods.

In some aspects, a system includes a processing system configured for use with a first catheter configured for insertion into an organ in a patient's body and comprising three or more sets of current injecting electrodes, one or more additional catheters configured for insertion into the organ in the patient's body and comprising one or more measuring electrodes, and an electronic control system coupled to the first catheter and the one or more additional catheters and configured to cause current to flow between each set of current-injecting electrodes and measure an electrical signal in response to the current flow caused by each set of current injecting electrodes at each of the measuring electrodes on the one or more additional catheters. The processing system is configured to be coupled to the electronic system and configured to determine the position of the each of one or more of the one or more current measuring electrodes relative to the first catheter based on the measured signals from the one or more measuring electrodes.

In some embodiments, the system can further include one or more of the first catheter: the one or more additional catheters; and the electronic control system.

Embodiments of the system may also include any features described herein in connection with the various methods.

In some aspects, a computer program product residing on a computer readable medium includes instructions for causing a computer to cause current to flow between each of three or more sets of current-injecting electrodes on a first catheter inserted into an organ in a patient's body, the organ having a periphery, in response to current flow caused by each set of current injecting electrodes, measure an electrical signal at each of one or more measuring electrodes located on one or more additional catheters inserted into the organ in the patient's body, and determine the position of each of one or more of the measuring electrodes on the additional catheters relative to the first catheter based on the measured signals from the one or more measuring electrodes.

Embodiments of the computer program product may also include instructions for causing a computer or system to perform any features described herein in connection with the various methods.

In some aspects, a computer program product residing on a computer readable medium includes instructions for causing a computer to determine locations of multiple tracked elements within an organ, the organ having a periphery at least three of the tracked elements being secured to fixed locations within the organ, determine the location of one or more other tracked elements relative to the at least three tracked elements secured to the fixed locations within the organ, and use the locations of the at least three tracked elements secured to the fixed locations within the organ to determine the locations of the one or more other tracked elements relative to a surface of the organ.

Embodiments of the computer program product may also include instructions for causing a computer or system to perform any features described herein in connection with the various methods.

In some aspects, a computer program product residing on a computer readable medium includes instructions for causing a computer to cause current to flow between each set of at least three sets of current-injecting electrodes on a first catheter, receive data relating to a measurement of an electrical signal measured in response to the current flow caused by each set of current injecting electrodes at each of the measuring electrodes on the one or more additional catheters, and determine the position of the each of one or more of the one or more current measuring electrodes relative to the first catheter based on the measured signals from the one or more measuring electrodes.

In some aspects, a system includes a control system configured to cause current to flow between each of three or more sets of current-injecting electrodes on a catheter within an organ in a patient's body. The system is further configured to receive data related to electrical signals measured at each of one or more measuring electrodes located on one or more additional catheters inserted into the organ in the patient's body. The system also includes logic (e.g., hardware or software) to determine the position of each of one or more of the measuring electrodes on the additional catheters relative to the first catheter based on the data related to the measured signals from the one or more measuring electrodes.

The system can also receive data relating to measured electrical signals from the multiple measuring electrodes on the first catheter and the logic for determining the relative position between the first catheter and each of the one or more of the measuring electrodes on the one or more additional catheters can be based on the measured signals for the measuring electrodes on the first catheter and the one or more additional catheters.

The logic for determining the relative position can associate each measured signal with a homogeneous component that depends on the relative position of each signal measuring electrode with respect to each set of current injecting electrodes and an inhomogeneous component associated with the periphery of the organ. The inhomogeneous component can be modeled as a variation in electric potential along a surface enclosing at least the first catheter that depends on the relative positions between the current injecting electrodes and the signal measuring electrodes. The logic for determining the relative position can additionally account for and/or determine an estimate for conductivity inside the organ. The logic for determining the relative position can additionally account for and/or determine a change in conductivity at the organ's periphery.

In general, the system can be used in various organs of the body. For example, the system can be used in relation to a patient's heart.

The logic for determining the relative position can additionally associate each measured signal with a homogeneous component and an inhomogeneous component associated with the organ's periphery. The system can further include the first catheter which is electrically connected to the system. The first catheter can include more than 32 measuring electrodes. The logic for determining the relative position can additionally use predetermined information about the relative positions of the electrodes on the first catheter. This information can be received by the system or programmed by a user of the system.

The logic for determining the relative position can additionally be based on an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter and the change in conductivity at the organ's periphery.

The logic for determining the relative position can additionally be based on an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter and the estimate for conductivity inside the organ.

The logic for determining the relative position can additionally be based on an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter, the change in conductivity at the organ's periphery and the estimate for conductivity inside the organ.

The system can use the data received from the multiple signal measuring electrodes on the first catheter to measure cardiac signals.

The system can further receive data relating to measurements from at least three electrodes to be used for reference that are secured to fixed locations within the organ. The electrodes used for reference can be measuring electrodes and the method further comprises determining the position of each of the electrodes used for reference relative to the first catheter. The at least three electrodes used for reference can be on a single catheter.

The system can further include logic for displaying the position of the one or more additional catheters relative to the surface of the organ. The system can also include a display.

The system can further include logic for using the determined position of each of the reference electrodes relative to the first catheter to determine a location of the first catheter relative to the surface of the organ. The system can further include logic for displaying the position of the first catheter relative to the surface of the organ. The system can further include logic for determining a position of each of the reference electrodes relative to the first catheter and determining a location of each of the one or more electrodes on the one or more additional catheters relative to the surface of the organ. The system can further include logic for correcting a location of the one or more additional catheters based on a movement of the organ, translation of the organ, a rotation of the organ, a movement caused by respiration, and/or a movement caused by movement of the patient.

The system can further include logic for determining a location of each of the one or more electrodes on the second catheter relative to the surface of the organ comprises correcting a location of each of the one or more electrodes on the second catheter based on a movement of the first catheter. The system can further include logic for generating a fixed coordinate system relative to a surface of the organ based on the information received from reference electrodes. The system can further include logic for determining the position of each of the one or more measuring electrodes on the second catheter relative to the surface of the organ. The system can further include logic for determining the position of each of the one or more the measuring electrodes on the second catheter relative to the surface of the organ by solving a minimization between the known locations of the reference electrodes relative to the organ and a determined position of each of the reference electrodes relative to the first catheter.

The system can further include a control system electrically connected to the first catheter to control the movement of the first catheter within the organ relative to the reference electrodes. The system can further include logic for tracking the position of the first catheter relative to the surface of the organ based on the measured signals on the first catheter and the fixed location of the reference electrodes. The system can further include logic for measuring cardiac signals. The system can also include one or more electrodes on the one or more additional catheters for delivering ablation energy for ablating tissue of the organ.

The system can further include a control system to control the movement of one or more of the additional catheters inside the organ and tracking the position of each of one or more measuring electrodes relative to the surface of the organ based on signals measured by the one or more measuring electrodes in response to current flow caused by each set of current injecting electrodes on the first catheter and the tracked position of the first catheter relative to the surface of the organ. The system can further include a control system to provide signals to cause an electrode to ablate selected regions of the cardiac chamber based on the measured signals and a tracked position of an electrode on the catheter used to ablate the selected regions.

The system can further include a control system to control the movement of an ablation catheter that includes an ablation electrode inside the organ and track the position of the ablation electrode on that catheter relative to the surface of the organ based on signals measured by the ablation electrode in response to current flow caused by each set of current injecting electrodes on the first catheter.

The system can further include logic to modulate the current caused to flow between each of the three or more sets of current-injecting electrodes in one or more of time and frequency.

The system cam repeat the determination of the relative position between the first catheter and the one or more electrodes on the one or more additional catheters multiple times during the patient's cardiac cycle.

The methods (including all methods described herein) and systems can be implemented using various hardware and/or software configurations. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer programs can include instructions stored on a computer readable medium. The instructions can include instructions to cause the system and/or one or more devices connected to the system (e.g., catheters) to perform the functions described here.

Embodiments of the system may also include devices, software, components, and/or systems to perform any features described above in connection with the first method and/or described below in connection with the second method.

In some aspects, a system can include, an electronic control system in electrical communication with a first catheter that is within an organ in a patient's body that includes three or more sets of current injecting electrodes. The system can also be in electrical communication with one or more additional catheters that include one or more measuring electrodes. The system can be configured to cause current to flow between each set of current-injecting electrodes and measure an electrical signal in response to the current flow caused by each set of current injecting electrodes at each of the measuring electrodes on the one or more additional catheters. The system can include a processing system coupled to the electronic system and configured to determine the position of the each of one or more of the one or more current measuring electrodes relative to the first catheter based on the measured signals from the one or more measuring electrodes.

Embodiments of the system may also include devices, software, components, and/or systems to perform any features described above in connection with the first method and/or described below in connection with the second method.

Embodiments of the methods and systems generally disclosed herein can be applied to determining the position of any object within an organ in a patient's body such as the patient's heart, lungs, brain, or liver.

As used herein, the "position" of an object means information about one or more of the 6 degrees of freedom that completely define the location and orientation of a three-dimensional object in a three-dimensional coordinate system. For example, the position of the object can include: three independent values indicative of the coordinates of a point of the object in a Cartesian coordinate system and three independent values indicative of the angles for the orientation of the object about each of the Cartesian axes; or any subset of such values.

As used herein, "heart cavity" means the heart and surrounding tissue.

Unless otherwise defined, all technical and scientific terms used herein have the same meaning as commonly understood by one of ordinary skill in the art to which this invention belongs. In case of conflict with documents incorporated herein by reference, the present document controls.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 16 is a flow diagram of an exemplary embodiment for cardiac mapping using a multi-electrode catheter.

DETAILED DESCRIPTION

Overview

Figure 1:
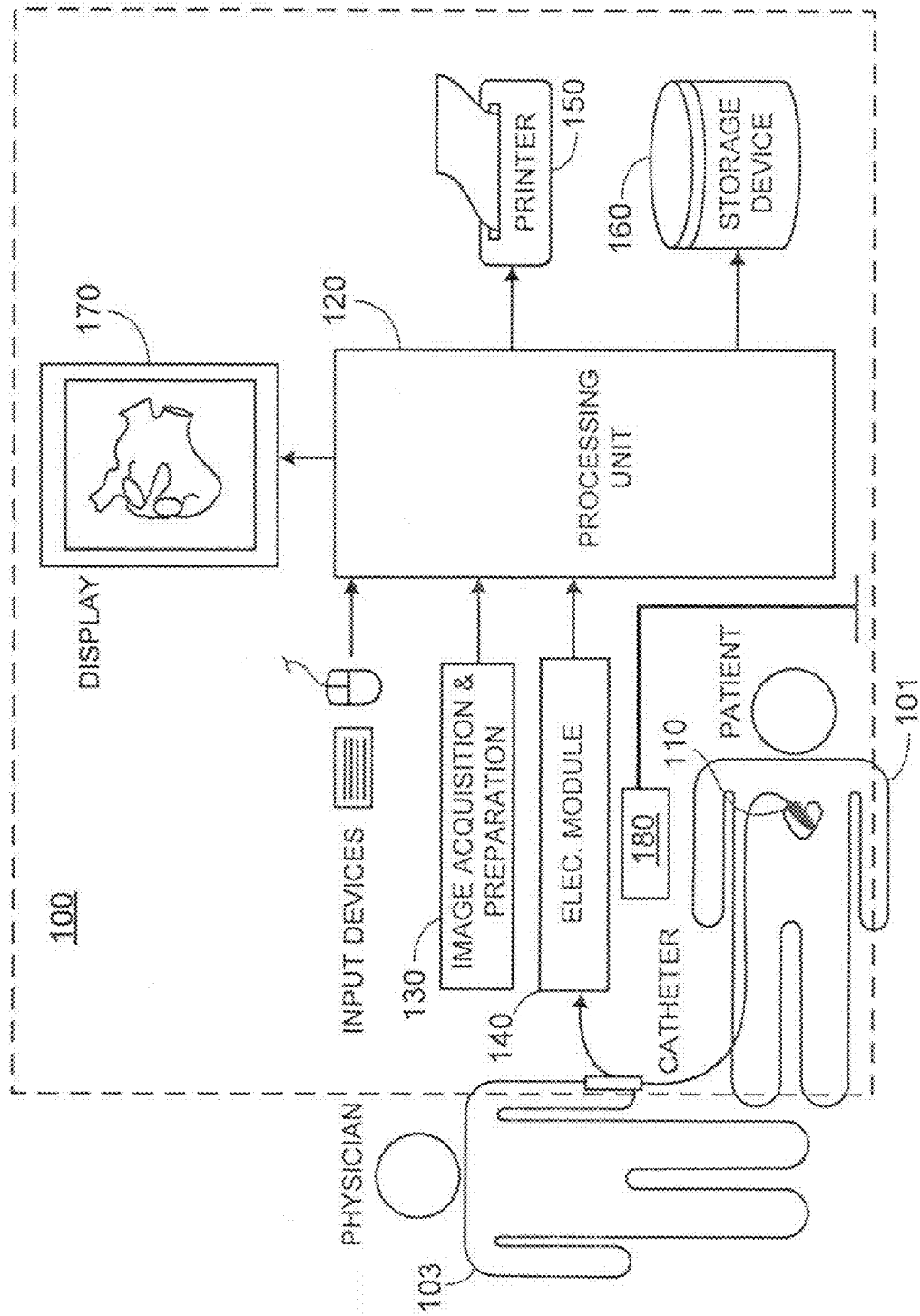
FIG. 1 is a schematic diagram of an exemplary system.

Embodiments disclosed herein include a method and system for determining the position of a catheter in a patient's heart cavity. More particularly, the methods and systems described herein provide a method for tracking a multi-electrode array (MEA) catheter, as well as additional electrodes mounted on other catheters, within and relative to the cardiac cavity, including any number of chambers within this cavity and the blood vessels surrounding it. Electrodes can be mounted on one or multiple catheters and by tracking these electrodes the location of such catheters can be determined and the catheters can be tracked. By knowing the physical characteristics of a catheter and the position of the electrodes on it, it is possible to track specific portion of the catheter (e.g. the tip) or to determine the shape and the orientation of the catheter (e.g. by using a spline fitting method on the location of multiple electrodes of the same catheter). Electrodes can also be mounted on other devices that require tracking inside the heart cavity. The tracking is accomplished by generating a multitude of electrical fields on the MEA catheter, using measurements of these generated fields on the MEA catheter to provide a calibration of chamber conductivity and a correction for inhomogeneity in the medium, and using measurements of the same fields on electrodes mounted on other catheters to locate them relative to the MEA.

The catheter may be configured with multiple electrodes and used for cardiac mapping, such as described in commonly owned patent application Ser. No. 11/451,898, entitled "NON-CONTACT CARDIAC MAPPING, INCLUDING MOVING CATHETER AND MULTI-BEAT INTEGRATION" and filed Jun. 13, 2006, application Ser. No. 11/451,908, entitled "NON-CONTACT CARDIAC MAPPING, INCLUDING PREPROCESSING" and filed Jun. 13, 2006, application Ser. No. 11/451,871 entitled "NON-CONTACT CARDIAC MAPPING, INCLUDING RESOLUTION MAP" and filed Jun. 13, 2006, application Ser. No. 11/672,562 entitled "IMPEDANCE REGISTRATION AND CATHETER TRACKING" and filed Feb. 8, 2007, and application Ser. No. 12/005,975 entitled "NON CONTACT MAPPING CATHETER" and filed Dec. 28, 2007, the contents of which are incorporated herein by reference. Generally, cardiac mapping involves determining information about the electrical activity of a patient's heart (e.g., at different locations of the endocardium surface) based on electrical signals (e.g., cardiac signals) measured by the multiple electrodes of the catheter. To perform such cardiac mapping, the position of the catheter (or more generally the positions of the catheter electrodes) within the heart cavity should be known.

To determine the position of the catheter in the patient's heart cavity, certain embodiments disclosed herein cause electrical current to flow within the heart cavity. The current originates from electrodes on the catheter internal to the heart cavity. The potential fields generated by the injected current will depend on the conductivity profile within the heart cavity. For example, blood and heart muscle have different conductivities. The potential fields are measured at multiple locations within the heart cavity. For example, electrodes on the catheter can be used to measure the potentials. The potentials measured by the electrodes on the catheter will depend on the position of the catheter within the heart cavity. Moreover, when current is injected from one or more electrodes on the catheter, the resulting potential fields will also depend on the position of the catheter within the heart cavity. Accordingly, measurements made by the catheter electrodes can be used to infer information about the position of the catheter in the heart cavity.

In some embodiments, potentials measured in response to the injected current (e.g. tracking signals) can be used to continuously monitor the position of one or more catheters in the heart cavity, even as they are is moved within the heart cavity.

In the above discussion and in the details that follow, the focus is on determining the position of one or more catheters in a heart cavity for diagnosis and treatment of cardiac arrhythmias. However, this is only an exemplary application. The method and system generally disclosed herein could be used to track essentially any catheter mounted with at least one electrode, regardless of the catheter's intended function. Relevant examples include endocardial biopsies, therapies involving intra-myocardial injections of cells, drugs, or growth factors, and the percutaneous placement cardiac valves. In other cases, the method and systems generally disclosed herein can be applied to determining the position of any object within any distribution of materials characterized by a conductivity profile. For example, the methods and systems generally disclosed herein can be applied to determining the position of any object within an organ in a patient's body such as the patient's heart, lungs, brain, or liver.

Furthermore, while in some of the specific embodiments that follow the signals measured by the object electrodes correspond to the relative strength (i.e., amplitude) of the measured electrical signal (e.g., potential), further embodiments may also analyze the phase of the measured signal, either alone or in combination with the amplitude of the measured signal. The phase of the measured signal is indicative of spatial variations in the imaginary part of the complex conductivity (e.g., permittivity) in the distribution of materials.

Representative System

FIG. 1 shows a schematic diagram of an exemplary embodiment of a system 100 to facilitate the tracking of a catheter 110 (or multiple catheters) inside the heart cavity of a patient 101. The catheter 110 is a moveable catheter 110 having multiple spatially distributed electrodes. The catheter (s) are used by a physician 103 to perform various medical procedures, including cardiac mapping and/or treatments such as ablation.

In some embodiments the catheter 110 is fitted with various types of electrodes that are configured to perform various functions. For example, the catheter 110 may include at least one pair of current injection electrodes ("CIEs") configured to inject electrical current into the medium in which the catheter 110 is disposed. The catheter 110 may also include multiple potential measuring electrodes ("PMEs") configured to measure the potentials resulting from the current injected by the current injection electrodes. In certain embodiments, the potential measuring electrodes are also used for cardiac mapping. In certain embodiments, the relative positions of multiple catheters disposed within the cardiac chamber can be determined based on signals measured by PMEs on the catheters. In certain additional embodiments, the positions of the catheters can be determined with respect to a surface of the organ (e.g., the heart).

Figure 2A:
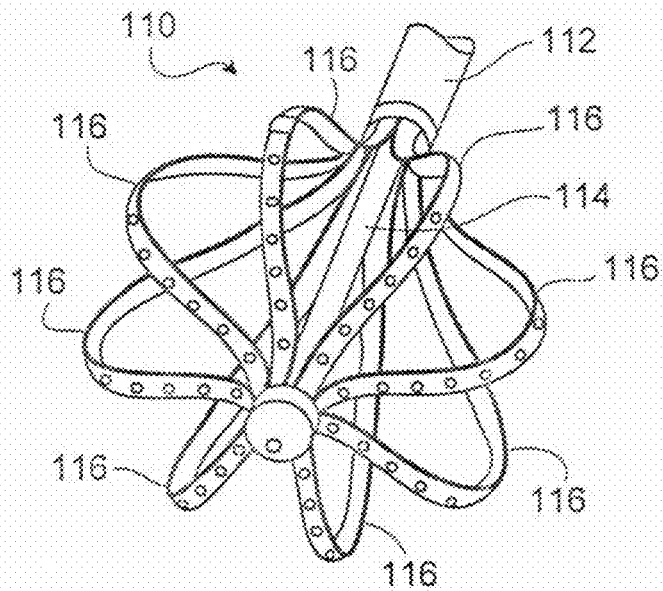
FIGS. 2a-2c show perspective, end, and side views, respectively, of a deployed catheter with multiple current injection electrodes (CIE) and multiple potential measuring electrodes (PME).
Figure 2B:
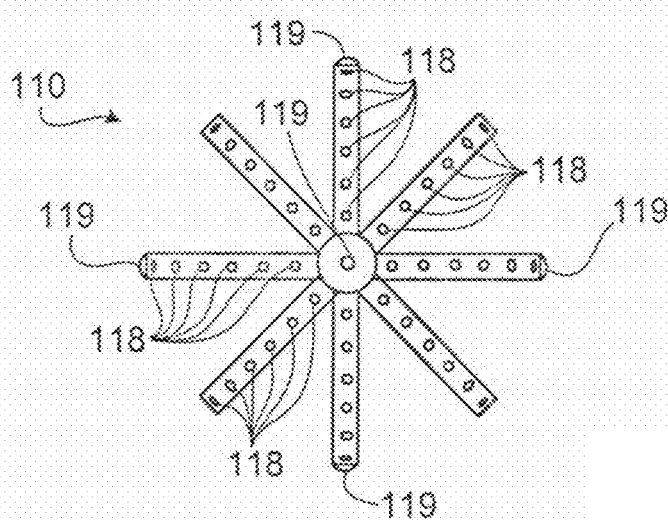
Figure 2C:
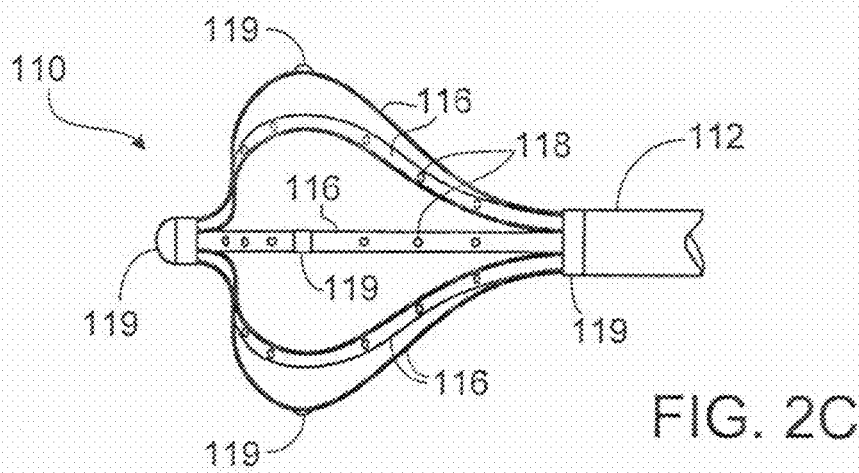

FIGS. 2a-c show different views for one embodiment of the catheter 110, which includes a base sleeve 112, a central retractable inner member 114, and multiple splines 116 connected to base sleeve 112 at one end and inner member 114 at the other end. When inner member 114 is in an extended configuration (not shown), splines 116 are pulled tight to the inner member so that catheter 110 has a narrow profile for guiding it through blood vessels. When inner member 114 is retracted (as shown in FIGS. 2*a-b*), splines 116 are deployed and pushed into an outward "olive" shaped configuration for use in the heart cavity. As explained in more detail below, the splines 116 each carry electrodes, so when the inner member is in the retracted configuration, the electrode are deployed in the sense that they are distributed over a greater volume.

Other known configurations may be used to deploy multi-electrode catheter 110 For example, the catheter may use a balloon, shape memory material such as Nitinol, or a polymer or other stiffening material to selectively deploy the catheter and its electrode into a desired configuration when in the patient's heart cavity. In further embodiments, the catheter geometry may be fixed, in which case it has the same configuration in the heart cavity as in the blood vessels leading to the heart cavity.

A number (>6) of current injecting electrodes (CIE) are mounted on catheter 110. A minimum of 3 CIE pairs are provided to span a 3D space and provide XYZ coordinates of other electrodes. For example, 3 orthogonal CIE pairs may be mounted on the catheter.

The CIE are designated 119, while electrodes 118 are used as potential measuring electrodes (PME). It should be appreciated that in order to inject current, an electrode must have a low enough impedance. Low impedance can be achieved by a sufficient surface area or by using materials or coatings that lower the impedance of the electrode. It should be noted that any low impedance electrode can be used for current injection and in a case where many or all electrodes are capable of injecting current the designation of such electrodes as CIE on the catheter only indicates that these electrodes are actually being used for current injection. It should be further appreciated that other configurations of CIE are possible as long as these configurations are known and can be accounted for in the field calculation process. Examples of such a configuration could be quadruples involving 4 CIE, or even a non-symmetrical configuration involving 3 CIE in known positions on the catheter. For simplicity the method using electrode pairs will be explained, but the same method can be applied using other configurations. In such cases there is still a need for at least 3 separate configurations in order to span the 3D space and provide XYZ coordinates of other electrodes.

Returning to the specific catheter embodiment of FIGS. 2*a-2c*, FIG. 2*a* shows a perspective view of catheter 110, FIG. 2*b* shows an end-on view of catheter 110, and FIG. 2*c* shows a side view of catheter 110, all with the catheter in its deployed configuration. Each spline includes multiple potential measuring electrodes (PME) 118, and every other spline includes a current injection electrode (CIE) 119 at its most-outward position. Current injection electrodes (CIE) 119 are also included on sleeve 112 at the base of the splines and on the front tip of inner member 114 where the splines meet. Accordingly, in the presently described embodiment, there are three pairs of CIEs, each generally defining one axis in a Cartesian coordinate system.

The purpose of the CIEs is to inject current into the heart cavity. For example, each CIE pair can define a source and sink electrode, respectively, for injecting current into the heart cavity. More generally, however, current may be injected in the heart cavity from multiple electrodes relative to a ground electrode. The purpose of the PMEs is to measure potentials in the heart cavity in response to the current provided by the CIEs. The PMEs can also be used for cardiac mapping.

In preferred embodiments, the current injecting electrodes 119 are generally mounted at different regions of the catheter 110 so as to maximize the information collected by multiple configurations. CIE pairs that are oriented orthogonally relative to each other produce less correlated measurements, which in turn increase resolution. In addition, electrode pairs that are distant from each other also produce less correlated measurements which increase resolution. This is why in the preferred embodiment of catheter 110 shown in FIGS. 2*a*-2*c*, the CIE electrodes 119 are aligned as pairs on three orthogonal axes.

In some embodiments, like that shown in FIGS. 2*a*-2*c*, multiple CIE electrode pairs are employed so that a large sample of measured potentials in the heart cavity can be obtained to thereby improve the robustness and accuracy of the tracking procedure. At some given time, any two electrodes from the CIE electrodes can be selected and activated so that one of the selected electrodes acts as the source electrode and the other electrode acts as a sink electrode. A control mechanism in electrical communication with the CIEs enables selection of any two electrodes to serve as the activated source/sink pair at a particular time. After that selected pair has been activated, and the resulting potentials in the heart cavity are measured by the multiple potential measuring electrodes, the pair of CIEs can be deactivated, and another pair of CIEs is selected to cause another electric field to be formed inside the heart cavity. Thus, the control mechanism regulates the selection and activation of the CIEs to cause a temporal sequence of injected currents to be created at different time instances, which in turn results in a temporal sequence of different electric fields formed inside the heart chamber in which the catheter 110 is deployed. The control mechanism electrically couples a signal generator to the selected electrodes. Selection of the particular electrodes to be activated can be based on a pre-determined sequence that is stored in a memory module connected to a central processor connected to the catheter 110, or it can be based on user-controlled signals that are electrically relayed to the control mechanism to cause the desired activation of the CIEs. Moreover, in further embodiments, more than a single pair of CIEs can be simultaneously activated to inject current into the heart cavity.

Referring again to FIG. 1, system 100 includes an electronics module 140 coupled to processing unit 120 for controlling the electrodes on catheter 110, including a signal generation module for injecting current into the heart cavity through the CIEs and a signal acquisition module for measuring potentials through the PMEs. The electronics module 140 can be implemented using analog or digital electronics, or a combination of both. Such exemplary configurations, which are intended to be non-limiting, are now described.

Figure 3:
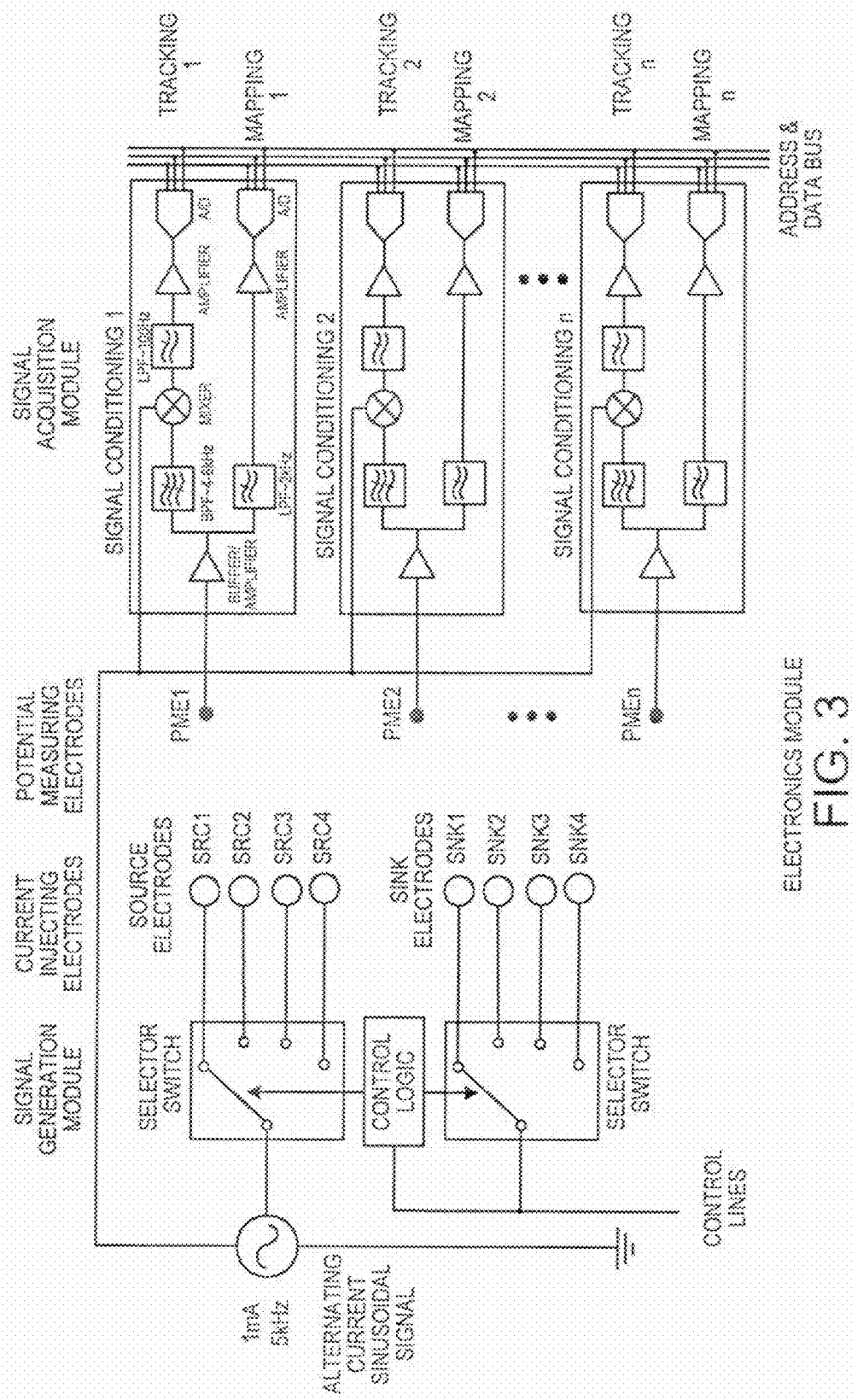
FIG. 3 is a schematic diagram of an analog implementation of a signal generation module (SGM) and signal acquisition module (SAM) for an electronics module coupled to the multi-electrode catheter.

Referring to FIG. 3, the signal generation and acquisition modules are implemented using analog hardware. The signal generation module (SGM) depicted supports 8 CIEs defining 4 source/sink electrode pairs, where SRC refers to a source electrode and SNK refers to a sink electrode. For the purpose of this example, each pair is driven using a 5 kHz oscillating 1 mA current source. Other driving frequencies, for example, 10 kHz, can be used. A selector switch is used to select each of the pairs sequentially based on control signals provided by the processing unit or other control logic. Each channel in the signal generation module is connected to a current injecting electrode. In this case the source and sink electrodes are pre-selected permanently such that each electrode is always either a source or a sink, although this need not be the case in other embodiments The signal acquisition module (SAM) buffers and amplifies the signals as they are collected by the potential measuring electrodes. The buffer prevents the acquisition system from loading the signals collected by the electrodes. After buffering and amplification, the signals are split and filtered into two channels, one for detecting the tracking signal (i.e., the signals produced in response to the CIEs) and one for detecting the signal generated by the heart's electrical activation (i.e., cardiac mapping). Because the heart's electrical activity (e.g., the cardiac signals) is primarily below 2 kHz, a low pass filter (LPF) is used to separate the cardiac mapping potential signals from those produced in response to the CIEs. The low pass filter may be implemented as an active filter responsible for both filtering and amplification. The signal is then sampled by an analog to digital converter. To support bandwidth and resolution requirements the converter may sample at >4 kHz at 15 bits per sample. After sampling, the signals are passed to the processing unit for further analysis. Both the LPF and A/D may be configured such that the filter and sample frequency can be changed by software control (not drawn).

The second channel following the input buffer detects the tracking signal (e.g., the signals measured in response to current injected by the CIE). In this embodiment, the detection is implemented using a lock-in amplifier approach to detect amplitude. It should be appreciated that other implementation can be used to accomplish the same task. In this channel the signal is first filtered using a band pass filter (BPF) whose pass band frequency is centered on the 5 kHz generated by the SGM. Following the BPF, the signal is multiplied by the same 5 kHz signal generated by the SGM using a mixer. As a result, the signal is down converted to DC such that its value following the down conversion is proportional to its amplitude before the down-conversion. The signal is then filtered using a very narrow LPF of roughly 100 Hz. The filter bandwidth has two effects. On the one hand, the narrower the filter the better noise performance will be. On the other hand, the wider the filter, the more tracking updates are available per second. A filter setting of 100 Hz provides excellent noise performance. After filtering, the signal is amplified and sampled by an analog to digital converter. The converter in this case may sample at 200 Hz using 15 bits per sample. After sampling, the signals are passed to the processing unit for further analysis. As before, the channel properties can be configured to be changed by software control (not drawn).

While the embodiment described above in relation to FIG. 3 described an analog signal generation and acquisition modules, in some examples a digital implementation can be used. For example, referring to FIG. 4, the signal generation and acquisition modules have a digital implementation. The SGM generates the required signals using an array of n digital to analog converters (D/A). In a preferred embodiment n=6. It should be appreciated that instead of n D/As it is possible to use fewer D/As and a multiplexed sample and hold amplifier. The signals generated by the D/As are controlled and timed by the processing unit. In one embodiment, the signals may mimic those described in the analog implementation whereby a sinusoidal signal is switched between electrodes. In other embodiments, however, the digital implementation provides more flexibility in that more complex signals (e.g. different frequencies, simultaneous activation of multiple electrodes) may be driven. After the conversion to an analog signal, the signals are buffered by an amplifier capable of driving the necessary current (<2 mA) at relevant frequencies (<30 kHz). After buffering, a processor controlled switch is used to support a high impedance mode. This is necessary in order to block a particular electrode from acting as a source or a sink at a particular time.

Figure 4:
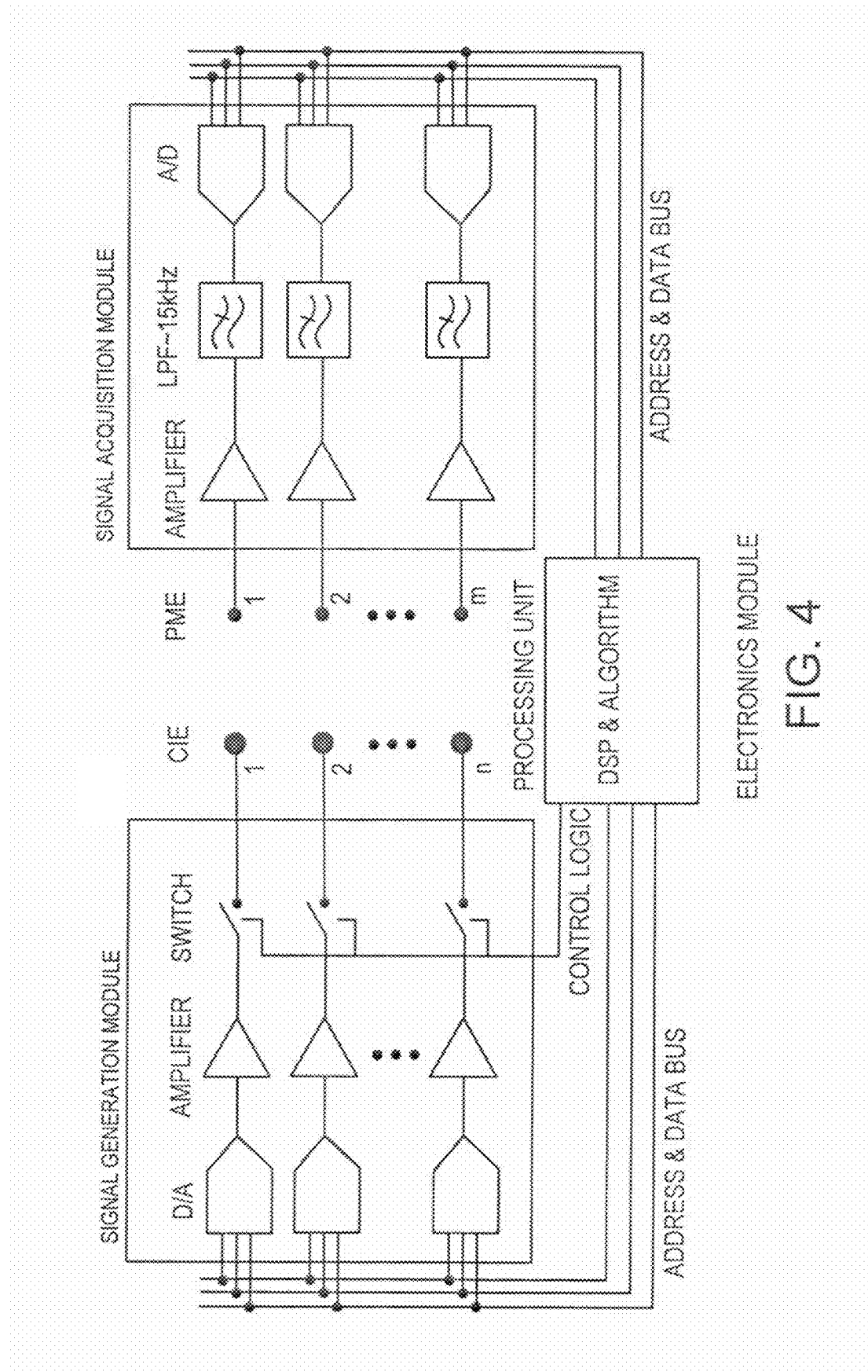
FIG. 4 is a schematic diagram of a digital implementation of a signal generation module (SGM) and signal acquisition module (SAM) for an electronics module coupled to the multi-electrode catheter.

In the SAM hardware, an input stage amplifies and buffers the signal. Following amplification the signal is low pass filtered in a wide enough band such that both the heart's electrical activity (<2 kHz) and signals generated by the SGM are kept inside the filtered band. In FIG. 4 the frequency band is 15 kHz. Following the filter, the signal is sampled above Nyquist frequency (>30 kHz) at 15 bits per sample. The sampled signals are then transferred to the processing unit which uses digital signal processing (DSP) techniques to filter the two channels in each electrode and down-convert the tracking signal appropriately.

A relatively small number of CIEs can result in a relatively large number of possible electrode pair combinations that can be activated to enable different potential field configurations to be formed inside the heart cavity, in which the catheter 110 is deployed and thus enhance the robustness of the tracking procedure. For example, six (6) electrodes mounted on the catheter 110 can be paired into fifteen (15) combinations of different source/sink pairs, thus resulting in fifteen different potential fields, for a particular potential value, formed inside the medium. As noted above, to achieve high robustness of the tracking procedure, the various source/sink electrodes disposed on the catheter 110 may be mounted at different regions of the catheter. For example, one useful configurations corresponds to that shown in FIGS. 2a-2c in which the six (6) CIEs include a pair of CIEs align along each of three orthogonal axes.

The potential measuring electrodes, configured to measure the electrical signals in the distribution of materials (e.g., the intracardiac blood) at the locations in which those electrodes are situated, are generally distributed substantially uniformly on the catheter 110. Preferably, the current injecting electrodes are designed to have low impedance at the interface between electrode and blood. The impedance between electrodes and blood is determined by the surface area of the electrode and electrode material. The larger the surface area, the lower the impedance In some embodiments, the electrodes can be similarly sized. For example, the potential measuring electrodes and the current injecting electrodes can each be configured to have a low enough impedance to function as a current injecting electrode. Providing similarly sized electrodes that can function as either potential measuring electrodes, current injecting electrodes, or both can provide an advantage of enabling more combinations and potential positions of the current injecting electrodes relative to the potential measuring electrodes.

In some additional embodiments, the potential measuring electrodes would have dimensions of 100 µm×100 µm, yielding a surface area of a surface area of 10,000 µm$^2$, while the current injecting electrodes would have dimensions of 1 mm×1 mm, yielding a surface area 1 mm$^2$. The larger surface area for CIEs is preferred in order to reduce their impedance at the interface to blood and allow the injection of current. The PMEs are less sensitive to blood interface impedance because they are performing the measurement with very high input impedance. Accordingly, reducing interface impedance for the PMEs is generally not as important as reducing it for the CIEs.

In some embodiments, specialized coatings such as Platinum Black, Iridium Oxide and Titanium Nitride may also be used to reduce impedance of electrodes for a given surface area. For example, such coatings may be applied to one or more of the CIEs, one or more of the PMEs, or all of the catheter electrodes.

In yet further embodiments, one or more of the electrodes on the catheters can be driven to function as both a CIE and a PME. For example, when it is desired to use an electrode as both PME and CIE, the electrode is connected to both a signal acquisition module and a signal generation module. For example, when the electrode is not used as a CIE to drive a current, the switch in the signal generation module corresponding to the respective electrode is opened. Accordingly, time division multiplexing schemes in the driving electronics of module can be used to operate a given catheter electrode as either a CIE or a PME. In yet another example, the electronics module can drive a given electrode so that it functions as a CIE at high frequencies and a PME at low frequencies (such as might be useful for cardiac mapping.)

In some embodiments, sixty-four (64) potential measuring electrodes are used. The exact number of potential measuring electrodes that are employed depends on the dimensions of the catheter 110 and on the desired accuracy of the tracking procedure.

As noted above, the PMEs on catheter 110 can also used for cardiac mapping, such as that described in commonly owned patent application Ser. No. 11/451,898, entitled "NON-CONTACT CARDIAC MAPPING, INCLUDING MOVING CATHETER AND MULTI-BEAT INTEGRATION" and filed Jun. 13, 2006, the contents of which are incorporated herein by reference. As also noted above, because the frequency of the current injected by CIEs (e.g., 5 kHz) is much higher than the frequency of the electrical activity of the patient's heart (e.g., the frequency of the cardiac signals), the signal acquisition module can separate signals measured by the PMEs based on frequency to distinguish tracking signals measured in response to currents injected by the CIE from cardiac mapping signals (e.g., frequencies higher than 2 kHz, and lower than 2 kHz, respectively.) Furthermore, in additional embodiments, catheter 110 may include separate electrodes used only for cardiac mapping.

The system 100 further includes the processing unit 120 which performs several of the operations pertaining to the tracking procedure, including the determination of catheter electrode locations that result in the best fit between the measured signals and those calculated for different positions of the catheter. Additionally, the processing unit 120 can subsequently also perform the cardiac mapping procedure, including a reconstruction procedure to determine the physiological information at the endocardium surface from measured signals, and may also perform post-processing operations on the reconstructed physiological information to extract and display useful features of the information to the operator of the system 100 and/or other persons (e.g., a physician). For example, the system 100 can display the location of the catheter(s) relative to a surface of the heart. In some embodiments, a stabilized representation of the heart and position can be used to display the position of the catheter as the shape of the heart changes during the heart's cycle.

The signals acquired by the various electrodes of catheter 110 during the tracking and/or the mapping procedure are passed to the processing unit 120 via electronics module 140. As described above, electronics module 140 can be used to amplify, filter and continuously sample intracardiac potentials measured by each electrode.

In some embodiments, the electronics module 140 is implemented by use of integrated components on a dedicated printed circuit board. In other embodiments, some of the signal conditioning tasks may be implemented on a CPU, FPGA or DSP after sampling. To accommodate safety regulations, the signal conditioning module is isolated from high voltage power supplies. The electronics module is also protected from defibrillation shock, and interference caused by nearby pacing or ablation.

The processing unit 120 shown in FIG. 1 is a processor-based device that includes a computer and/or other types of processor-based devices suitable for multiple applications. Such devices can include volatile and non-volatile memory elements, and peripheral devices to enable input/output functionality. Such peripheral devices include, for example, a CD-ROM drive and/or floppy drive, or a network connection, for downloading related content to the connected system. Such peripheral devices may also be used for downloading software containing computer instructions to enable general operation of the respective unit/module, and for downloading software implemented programs to perform operations in the manner that will be described in more detailed below with respect to the various systems and devices shown in FIG. 1. Alternatively, the various units/modules may be implemented on a single or multi processor-based platform capable of performing the functions of these units/modules. Additionally or alternatively, one or more of the procedures performed by the processing unit 120 and/or electronics module 140 may be implemented using processing hardware such as digital signal processors (DSP), field programmable gate arrays (FPGA), mixed-signal integrated circuits. ASICS, etc. The electronics module 140 is typically implemented using analog hardware augmented with signal processing capabilities provided by DSP, CPU and FPGA devices.

As additionally shown in FIG. 1, the system 100 includes peripheral devices such as printer 150 and/or display device 170, both of which are interconnected to the processing unit 120. Additionally, the system 100 includes storage device 160 that is used to store data acquired by the various interconnected modules, including the volumetric images, raw data measured by electrodes and the resultant endocardium representation computed there from, the reconstructed physiological information corresponding to the endocardium surface, etc.

Tracking System

In general, a tracking system tracks the positions of multiple catheters relative to one another and/or tracks the position of one or more catheters relative to the surface of the heart. More particularly, measurements on PME on the MEA catheter calibrate for chamber conductivity and inhomogeneity and the system tracks additional electrodes mounted on different catheters using the signals emanating from the CIE.

Figure 5:
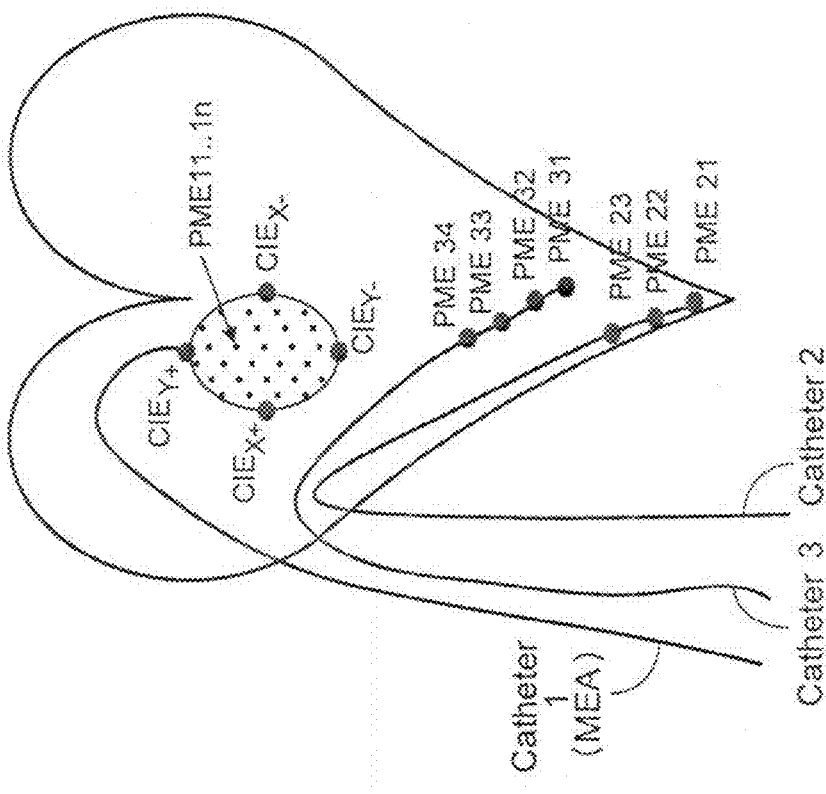

FIG. 5 shows an exemplary embodiment where three catheters (e.g., catheter 1, catheter 2, and catheter 3) each including multiple electrodes are positioned within a patient's heart. In this scenario, catheter 1 is the MEA mounted with both PME and CIE electrodes, while catheters 2 and 3 are mounted with a number of PME each.

The electrodes mounted on catheters 2 and 3 measure potentials emanating from cardiac activation, as well as potentials injected into the medium by the CIE. There is a need to distinguish between the two signals in order to separate the tracking signal measured by the PME in response to current injected by the CIE being used for the location determination from the cardiac signal being used for generating the electrical activation maps. The CIE on catheter 1 inject the current at a frequency higher than cardiac activation (cardiac activation<2 kHz, CIE>4 kHz, e.g. 5 kHz) such that the two types of signals can be distinguished using frequency analysis. It should be noted that other methods for distinguishing between the CIE signal and the cardiac activation signal can be used, such as injecting a spread-spectrum signal having a low energy level in the frequency range of the cardiac activation signal, and detecting this spread-spectrum signal in the signal collected by the all PME.

Figure 7:
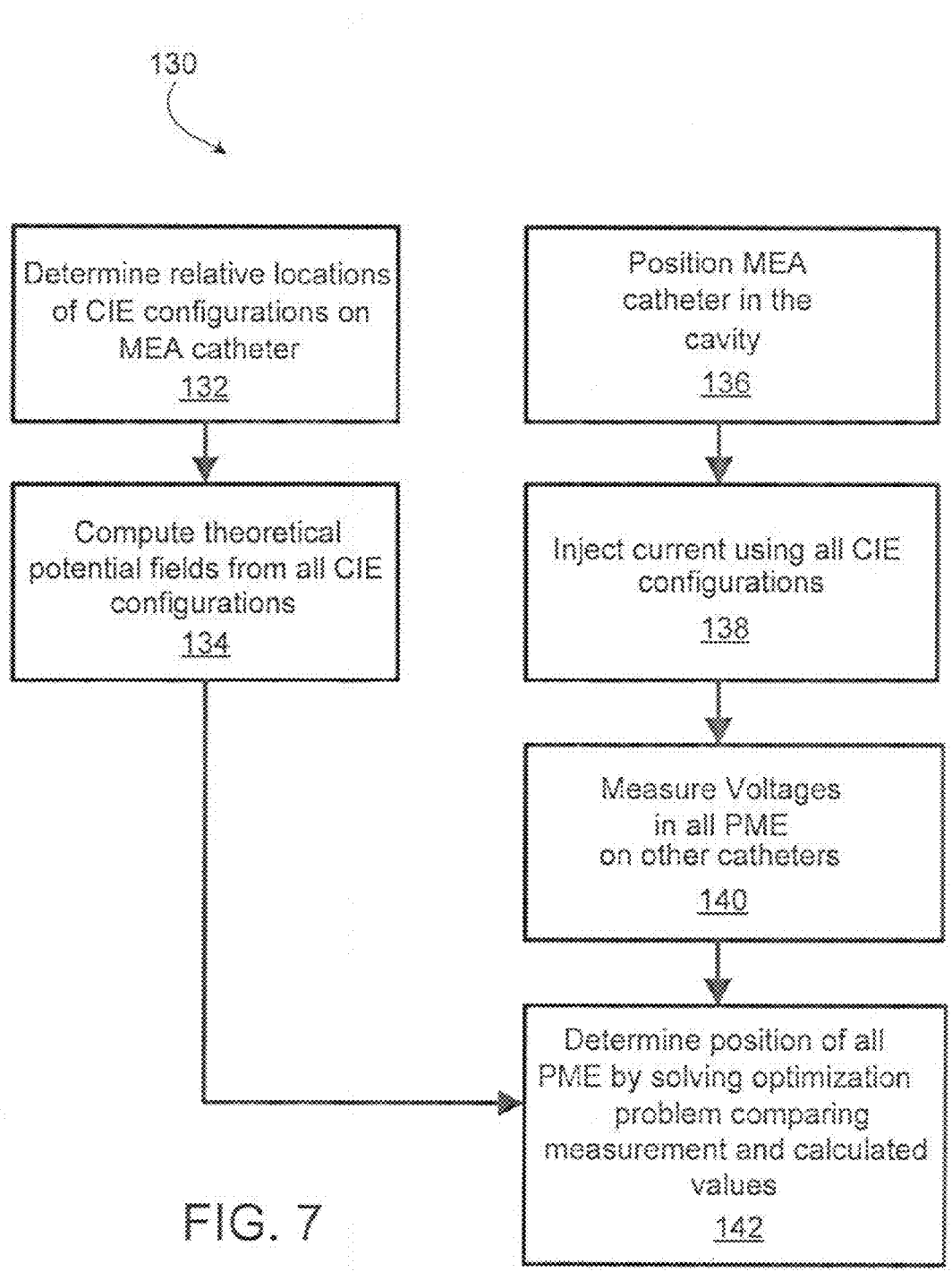
FIG. 7 is a flow diagram of an exemplary embodiment for determining the positions of PME.

FIG. 7 is a flow diagram providing a top-level depiction of a procedure 130 performed by the system 100 in the course of determining the location of PME.

In step 136, an MEA catheter (e.g., catheter 1 in FIG. 5) is positioned in the cavity. For example, the MEA catheter can be positioned within the heart cavity. For example, the MEA catheter can be inserted into the heart chamber via a suitable blood vessel leading to the heart chamber. The locations of the CIE and PME on the MEA are known. In some embodiments, the electrodes of the MEA catheter are bundled into a compact configuration that enables the MEA catheter to be delivered to the heart chamber with minimal obstruction. Once inside the heart chamber, the electrodes of the catheter are deployed into a specified electrode arrangement relative to the MEA catheter (e.g., to provide known relative locations of the CIE and PME). In some embodiments, the MEA catheter can be deployed into multiple, different specified electrode arrangements provided that the relative locations of the CIE and PME are known for each arrangement. In order to span the space 3 (or more) separate known configurations of CIE need to inject current. There is a need to determine the source of the injected signal (e.g., a source of a tracking signal measured by the PME in response to current injected by the CIE) in order to trace it to a specific CIE configuration. In step 138, the current injection electrodes on the MEA inject current using different CIE configurations. More particularly, a pair of CIEs is selected as a source/sink pair to inject current into the heart cavity. One of the electrodes of the selected pair serves as the source electrode, and accordingly that electrode is activated by applying a voltage source to the source electrode. The other electrode serves as the sink electrode, and is thus set to a lower potential level than the source electrode. The other sink/source electrodes disposed on the catheter are electrically deactivated and held at high impedance. The selected pair of source/sink electrodes thus becomes active and imparts current into the intracardiac blood medium in which the catheter is disposed resulting in the formation of potential fields in the medium. The 3 pairs of CIE inject the current sequentially, one pair at a time, so that it is possible to trace the source of the measured PME signals to a specific pair. This is called time division multiplexing. In the case of time division multiplexing, CIE are activated in sequence such that at one point in time one pair is activated (e.g., $CEI_{X+}$ and $CEI_{X-}$ as shown in FIG. 5) and at the next point in time another pair is activated (e.g., $CIE_{Y+}$ and $CIE_{Y-}$). The switching between pairs may occur every cycle (e.g., ⅕ kHz=200 µs) or every few cycles (e.g., 20 cycles, 20×200 µs=4 mS). In the 3D case there is at least an additional electrode pair mounted on the MEA catheter which may be perpendicular to the line created by $CEI_{X+}$ and $CEI_{X-}$ (e.g. on Z-axis as shown in FIG. 5). It should be noted that frequency or code division (spread spectrum) multiplexing, rather than time division may be used to separate the signals. In the case of frequency multiplexing all CIE pairs may inject the current at the same time, but each pair uses a different signal frequency. The signal collected at the PME is filtered according to the frequency, and the signal measured in each frequency is then associated with the appropriate originating pair. In response to current flow between the pair of selected source/sink electrodes, the PMEs distributed at multiple locations on the catheter measure, in step 140, the resultant potential field present at the those multiple locations. The measured potentials are recorded, along with other information associated with the measurement, including, for example, the identity and/or locations on the MEA catheter of the activated sink/source electrodes that imparted the current through the medium. The PME electrodes can be located on other catheters included within the cavity (e.g., catheters 2 and 3 in FIG. 5).

In a separate step, in step 132, the system determines the relative locations of the CIE configurations on the MEA catheter (e.g., catheter 1 in FIG. 5). For example, the locations of the CIE on the MEA catheter can be known based on the manufacture of the MEA catheter using a repeatable process that guarantees the MEA configuration. In such examples, determining the locations of the CIE can include accessing stored information about the known locations of the CIE. In step 134, the system computes theoretical potential fields from the CIE configurations. The theoretical potential fields provide expected computed measurements in a given location.

In step 142, the tracking of the electrodes on catheters 2 and 3 is performed by solving an optimization problem that compares the measurement collected by PME21 . . . PME23 or PME31 . . . PME34 as a result of activation of the CIE pairs, to expected computed measurements in a given location. The location that minimizes the difference between the computed and measured potentials is assigned as electrode location. The following description will cover the method for computing expected measurements, method for performing the optimization and method for generating and collecting signals.

Furthermore, while in some of the specific embodiments that follow the signals measured by the object electrodes correspond to the relative strength (i.e., amplitude) of the measured electrical signal (e.g., potential), further embodiments may also analyze the phase of the measured signal, either alone or in combination with the amplitude of the measured signal. The phase of the measured signal is indicative of spatial variations in the imaginary part of the complex conductivity (e.g., permittivity) in the distribution of materials.

The computation of expected measurements in a given location will first be described for a homogeneous case, followed by the necessary modifications for an inhomogeneous case.

Figure 6:
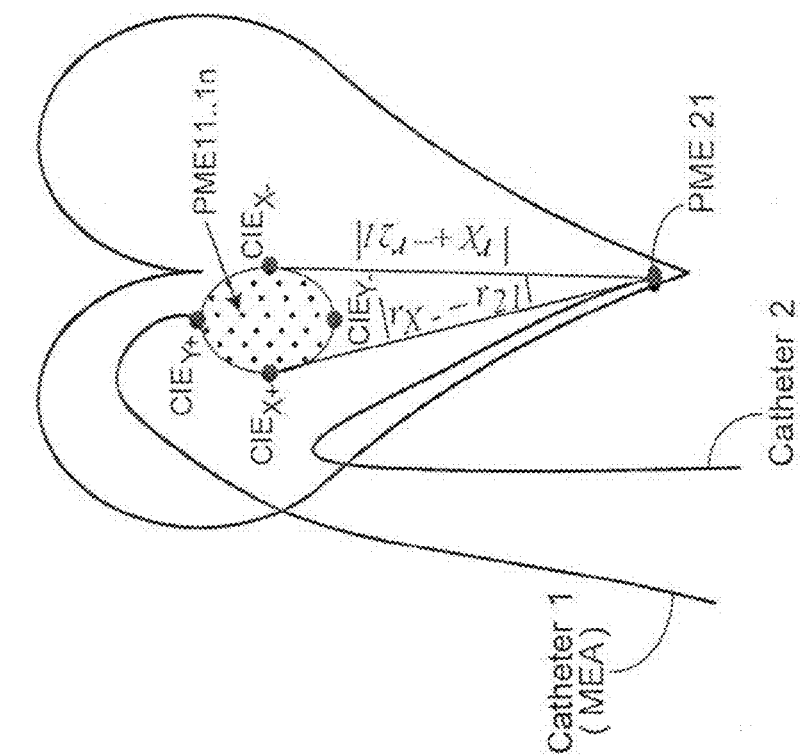
FIGS. 5 and 6 are exemplary schematic diagrams of arrangements for positioning current injection electrodes (CIE) and potential measuring electrodes (PME) with respect to a patient's heart cavity.

In a homogeneous medium with uniform conductivity $\sigma_h$, the expected measurements are computed by treating the CIE pairs as dipoles and solving the field propagation equation in the medium. For example, as shown in FIG. 6, assuming the amount of current injected by the pair $CIE_{X+}$ and $CIE_{X-}$ is $I_X$, the corresponding measurement on PME21 would be:

$$PME21, X = \frac{I_X}{4\pi\sigma_h}\left(\frac{1}{|r_{X+} - r_{21}|} - \frac{1}{|r_{X-} - r_{21}|}\right) \quad (1)$$

In this case, $|r_{X+}-r_{21}|$ is the distance between electrodes $CIE_{X+}$ and PME21 and $|r_{X-}-r_{21}|$ is the distance between $CIE_{X-}$ and PME21.

In this case, $\rho_{21}=(X_{21},Y_{21},Z_{21})$ is the location in 3D Cartesian coordinates for which the potential is being computed. In the case of three CIE pairs along three axis (X,Y,Z), three measurements ($V_{PME,X}$, $V_{PME,Y}$, $V_{PME,Z}$) will be obtained. Correspondingly, three computed results ($\hat{V}_{PME21,X}$, $\hat{V}V_{PME21,Y}$, $\hat{V}_{PME21,Z}$) will also be obtained for a specific location $\rho_{21}$ as described above. The value of an average empirical value can be used for $\sigma_h$ (e.g., 1/σ=1.6 Ωm). The specific location will be computed such that $\rho_{21}$ minimize the expression:

$$\rho_{21}{}^{min}|\Sigma_{i=X,Y,Z}(\hat{V}_{PME21X}-V_{PME21X})^2| \quad (2)$$

Equation (2) is a non-linear optimization problem. This problem can be solved using an iterative scheme such as Newton-Raphson or Levenberg-Marquardt or a direct search method such as the Nelder-Mead Simplex Method.

This method determines the location of PME without any calibration and any need for additional measurements on catheter 1.

Figure 8:
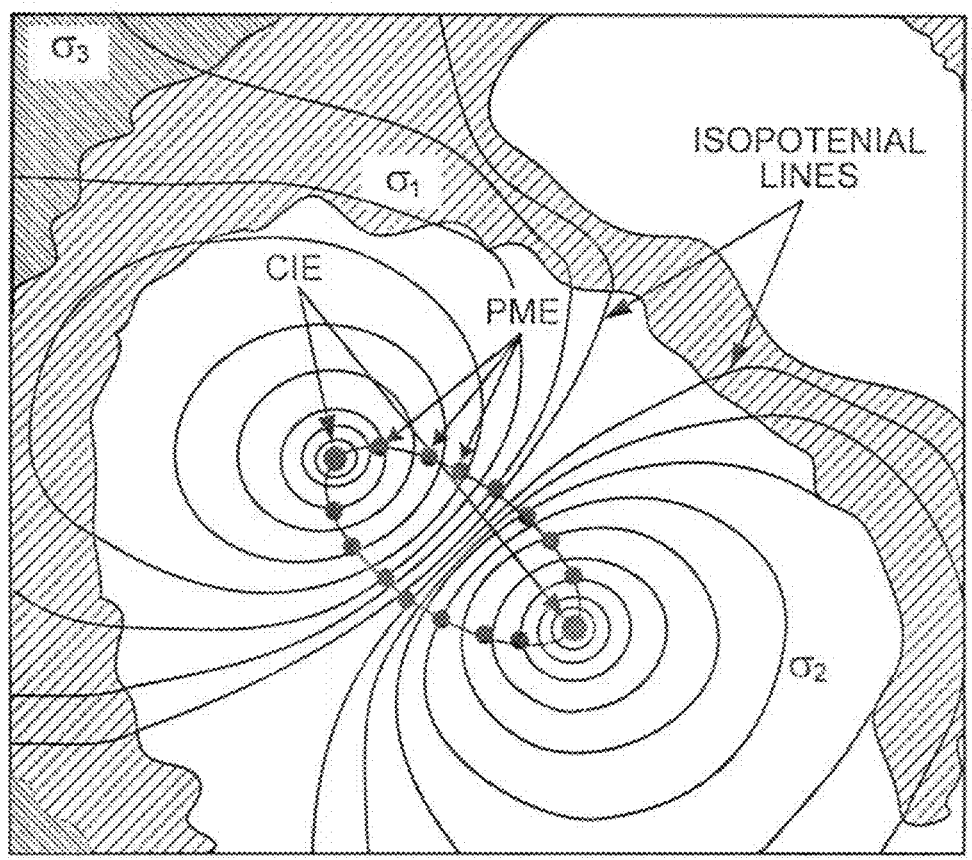
FIG. 8 is a schematic diagram of potential field lines produced by current injection electrodes (CIE) activated in a patient's heart cavity and the effect of an inhomogeneous medium on the resulting potential field.

While the method described above provides a process for determining expected measurements in a given location in a homogeneous medium, the heart chamber is not a homogeneous medium. Rather the periphery of the organ can include various objects surrounding the homogeneous blood medium that have different conductivities. For example, the periphery of the heart can include the walls of the heart, the lungs surrounding the heart, etc. FIG. 8 is a schematic diagram of potential field lines produced by current injection electrodes (CIE) activated in a patient's heart cavity, and potential measuring electrodes on a catheter used to measure the potential field at different locations to infer information about the position of the catheter within the heart cavity. As FIG. 8 shows, multiple conductivities exist in the medium. For example, the resistivity (1/conductivity) of intracardiac blood is approximately 1.6 $\Omega$m (1/$\sigma_2$), and the resistivity of the myocardium (1/$\sigma_1$) averages about 5.6 $\Omega$m. The heart is surrounded by the lungs whose resistivity (1/$\sigma_3$) is assigned 150 $\Omega$m.

Since the area surrounding the cardiac chamber is not homogeneous, accounting for the inhomogeneity in the computation of field propagation results in more accurate location determination for the tracked electrodes. While in some embodiments target accuracy requirements can be met using the estimates provided above assuming a homogenous medium, in some other embodiments if the effect of the medium's inhomogeneity is ignored, error introduced in the tracking process can exceed the target accuracy requirements. The locations of the PME relative to the CIE on the MEA are known and the measurements collected by the PME on the MEA, PME11...1n (e.g., n=64), are used in order to account for inhomogeneity in the expected computation. The same measurements are used in order further calibrate the value used for $\sigma_h$ so that no other assumptions are required.

The contribution to the field generated in blood volume can be separated into the contribution of the current dipole and that of the inhomogeneity at the organ's periphery (e.g., a homogenous component and an inhomogeneous component). The contribution of the current dipole is identical to the homogeneous case described above. Because blood is a homogenous medium without any sources other than the dipole, the contribution of the inhomogeneity can be modeled as a charge distribution outside the blood volume. This charge distribution gives rise to an unknown Dirichlet boundary condition, or voltage distribution, on any closed surface that exists inside the homogeneously conductive blood volume. For the purpose of the calculations, the closed surface does not need to be an actual, physical surface such as the surface of the heart (e.g., the heart wall), but can instead be a mathematically defined surface. In general, the surface is defined to include a large enough area to encompass the CIE and the PME on the catheters while still being contained within the blood volume.

Figure 9:
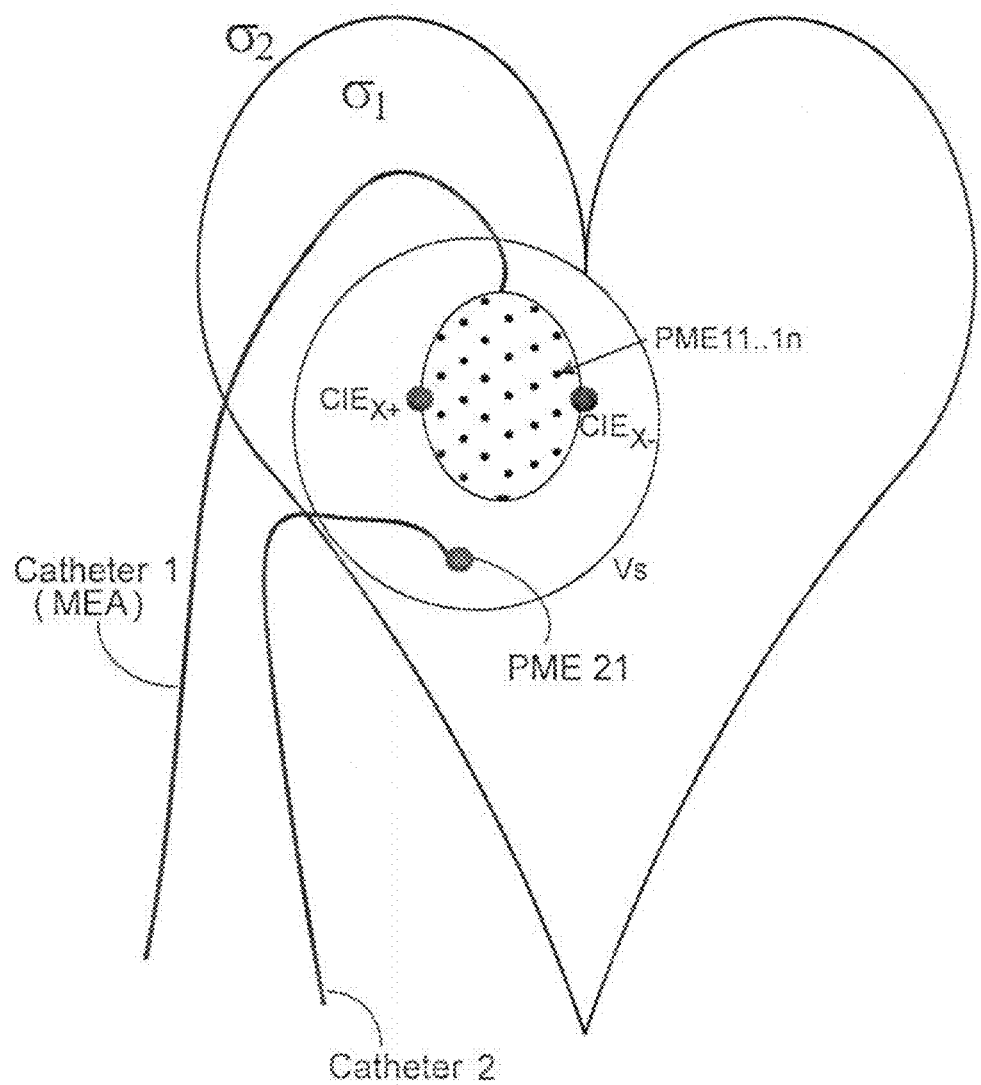
FIG. 9 is an exemplary schematic diagram of an arrangement for positioning current injection electrodes (CIE) and potential measuring electrodes (PME) with respect to a patient's heart cavity.

For example, FIG. 9 shows an example in which a spherical surface is defined that would have voltage distribution Vs representing the contribution of inhomogeneity. Since the contribution of the current dipole is accounted for separately, the field contribution due to inhomogeneity inside the volume contained by surface S follows Laplace's equation. In other words, the measurements collected by PME11...1n can be treated as a superposition of a field generated by a dipole in a homogeneous volume and propagation of the voltage distribution Vs from a surface S to the PMEs which follows Laplace's equation. It follows that the voltage distribution Vs, which represents the contribution of the inhomogeneity, can be computed using an inverse Laplace algorithm based on measurements collected by PME11.1n. In this manner, the medium's inhomogeneity outside the blood volume can be accounted for with no knowledge or assumptions of what that inhomogeneity is. The only assumption is that blood is homogeneous.

Figure 10:
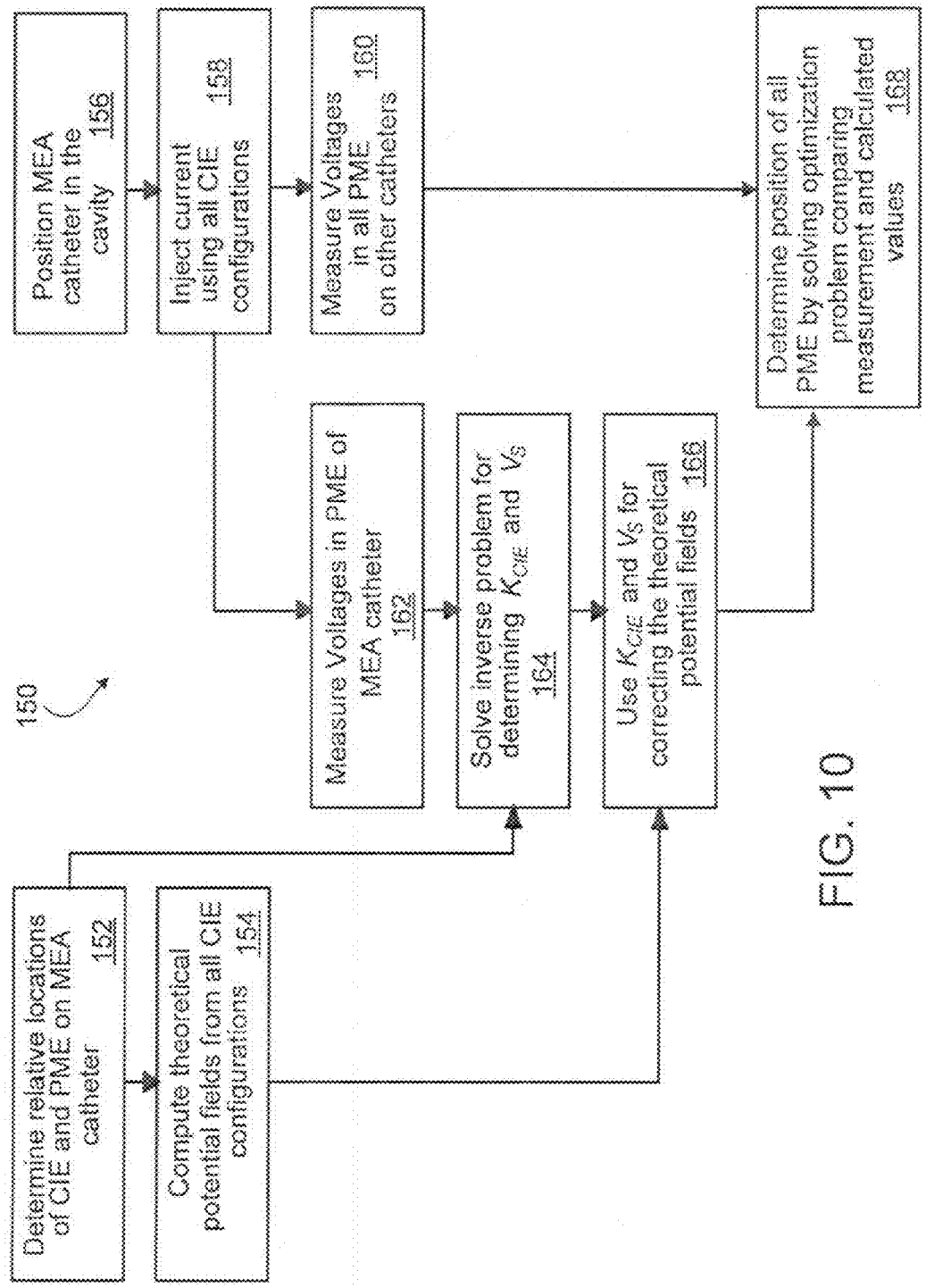
FIG. 10 is a flow diagram of an exemplary embodiment for determining the voltage at any location inside the blood volume using inverse theory.

FIG. 10 is a flow diagram providing a top-level depiction of the a procedure 150 performed by the system 100 to compute the voltage at any location inside the blood volume using inverse theory. This method determines the location of PME using a self calibrating procedure for improving the accuracy. To perform the computation a surface S is constructed that is contained in the blood volume and contains the point of interest. For example, in general, the surface S will include the CIE and PME on the MEA (e.g. catheter 1 in FIG. 5) and the PME on other catheters for which the locations are tracked (e.g., catheters 2 and 3 in FIG. 5).

The determination of the location of the PME is similar to the method described above in relation to FIG. 7 for the homogeneous case. One difference is that the computed results ($\hat{V}_{PME21,X}$, $\hat{V}_{PME21,Y}$, $\hat{V}_{PME21,Z}$) are obtained from a calibrated analysis that accounts for the different conductivities rather than the homogeneous analysis. The calibration is performed by using additional measurements on the MEA catheter (e.g., catheter 1).

In step 152, the system determines the relative locations of the CIE configurations on the MEA catheter and, in step 154, computes theoretical potential fields from the CIE configurations assuming a homogenous medium. The theoretical potential fields provide expected computed measurements in a given location if the medium were homogenous. As described below, these known locations of the CIE and PME and computed theoretical potential fields are used to determine corrected potential fields based on measurements at PME on the MEA.

In step 156, an MEA catheter that includes both CIE and PME in known locations is positioned in the cavity. For example, the MEA catheter can be positioned within the heart cavity. In step 158, the CIE on the MEA are used to inject current using the different CIE configurations. In step 162, the voltages on PME electrodes of the MEA catheter are measured. In step 164, the measured voltages and the known relative locations of the CIE and PME on the MEA catheter are used to solve the inverse problem for determining $K_{CIE}$ and $V_S$ (as described in more detail below). In step 166, the calculated values of $K_{CIE}$ and $V_S$ are used to correct the theoretical potential fields to account for the inhomogeneity. As such, the measurements on the MEA are used to calibrate the system to account for inhomogeneity.

In a separate step 160, the voltages on PME electrodes of the other catheters (e.g., catheters other than the MEA catheter) are measured. The measurements in steps 160 and 162 can be preformed concurrently based on the current injected by the CIE. In step 168, the position of the PME electrodes of the other catheters are determined by solving an optimization problem comparing the measured values at the PME electrodes and the calculated corrected values (e.g., the theoretical potential fields accounting for the inhomogeneity).

As noted above, in order to track the location of multiple catheters, measurements of PME on the MEA catheter are used to determine a contribution and correction to the potential fields based on inhomogeneity. One step is to model an observed voltage on the PME to account for both contributions due to a homogenous component and contributions due to the inhomogeneity. The forward operator includes a component related to the dipole and a component related to the inhomogeneity. The expected voltage of a PME can be represented by:

$$\hat{V}_{PME} = V_{IH} + V_{DIP} \quad (3)$$

Where $\hat{V}_{PME}$ is a vector containing the computed expected voltage collected by PME on the MEA (PME11 ... 1*n*), $V_{DIP}$ is a vector containing the contribution of the dipole for each electrode and $V_{IH}$ is a vector containing the contribution of the medium's inhomogeneity for each electrode. All three vectors have the dimension n×1 where n is the number of PME on the MEA (e.g., n=64).

$V_{DIP}$ can be represented in the following manner:

$$V_{DIP} = A_{DIP} \times K_{CIE} \quad (4)$$

$A_{DIP}$ is a matrix of size n×2 where the first column is $1/r_+$, where $r_+$ is the distance between the source dipole electrode and the PME electrode and the second column is $1/r_-$ where $r_-$ is the distance between the sink dipole electrode and the PME. $K_{CIE}$ is a 2×1 vector representing $$\begin{pmatrix} \frac{I_{CIE}}{4\pi\sigma} \\ -\frac{I_{CIE}}{4\pi\sigma} \end{pmatrix}$$

Figure 11:
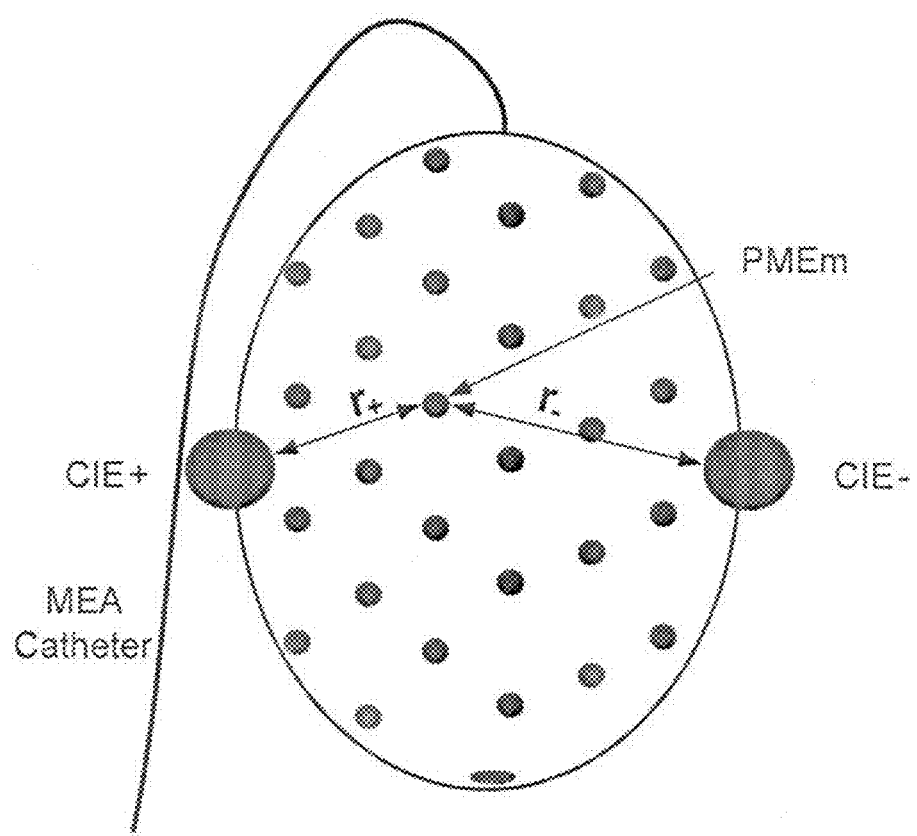
FIG. 11 is a schematic diagram of the distances between a source dipole electrode and the PME electrode and a sink dipole electrode and the PME electrode.

Since it is assumed that all current flows between two CIE, the two are mirrors of each other. As shown in FIG. 11, the relative locations between the CIE (e.g., CIE+ and CIE−) and the PME are also used to account for the bloods conductivity. $K_{CIE}$ rather than $I_{CIE}$ is used to avoid solving explicitly for $I_{CIE}$ and blood's conductivity σ.

The physical laws governing the reconstruction of the inhomogeneity information at the surface S are briefly summarized below:

The potential V in a homogeneous volume Ω is governed by Laplace's equation $$\vec{\nabla}^2 V = 0 \quad (5)$$

subject to boundary conditions $$V = V_s \text{ on surface } S \quad (6)$$

where S represents the surface for solving the inhomogeneity boundary condition.

Figure 12:
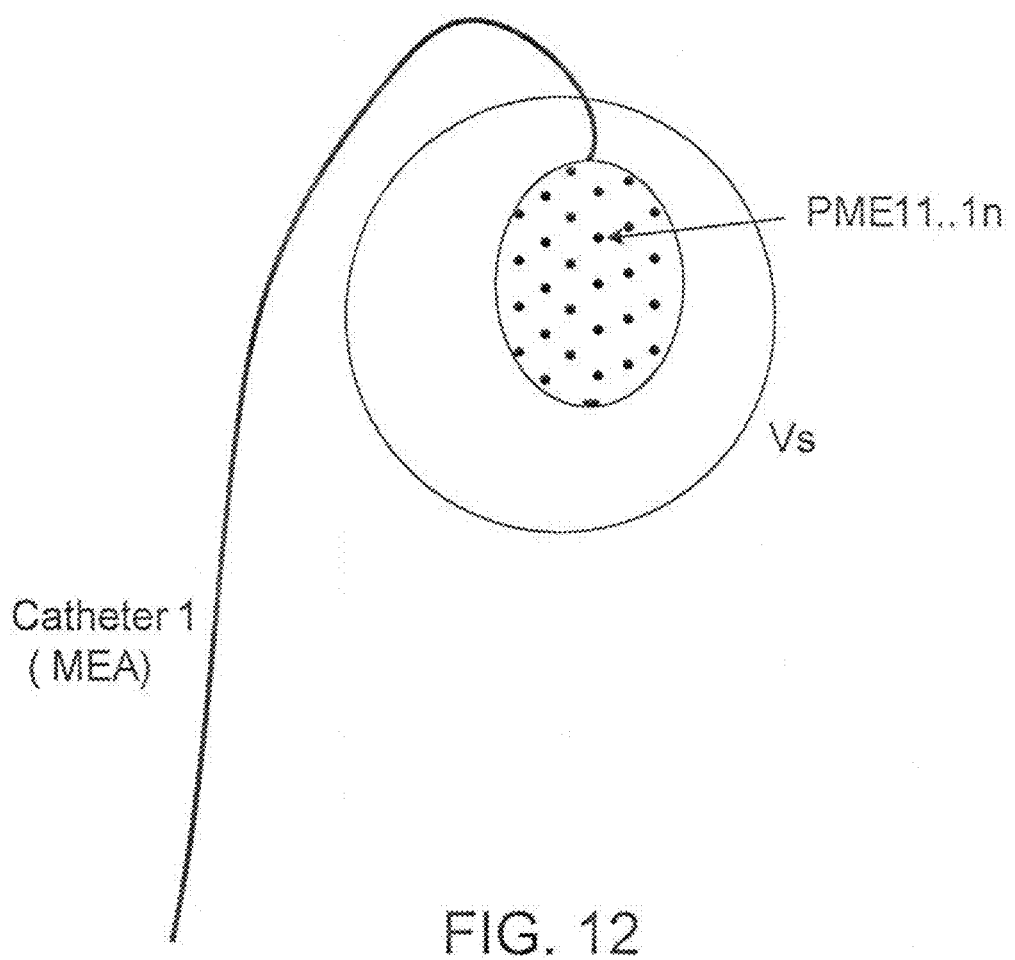
FIG. 12 is a schematic diagram of a catheter located within a surface S.

Numerical methods such as boundary element method (BEM), finite element method (FEM), finite volume method, etc. may be used to solve Laplace's equation. Since the surface S may be chosen such that it has an analytical representation, spherical harmonics may also be used. Each numerical method represents the geometry and signal using basis functions, but each method uses its own representation. In all numerical methods the potentials on the surface and on the PME are represented by finite-dimensional vectors. Since Laplace's equations are linear, these vectors are related by a matrix $A_{IH}$, known as the forward matrix:

$$V_{IH} = A_{IH} \times V_S \quad (7)$$

where $V_{IH}$ is a vector containing the field contribution of inhomogeneity measured by the PME on the MEA and $V_S$ is a vector containing the voltage distribution on surface S (e.g., as shown in FIG. 12). The matrix $A_{IH}$ has dimensions of n×m, where n is the number of PME electrodes on the catheter and in is the number of degrees of freedom in the surface potential, usually the number of surface elements used to represent the surface S. For example, the number of degrees of freedom (m) can be between about 500 and about 1500 (e.g., about 1000).

Using equations 4 and 7, equation 3 can be re-written as:

$$\hat{V}_{PME} = A_{IH} \times V_S + A_{DIP} \times K_{CIE} = [A_{IH} \; A_{DIP}] \begin{bmatrix} V_S \\ K_{CIE} \end{bmatrix} \quad (8)$$

For the construction of both $A_{DIP}$ and $A_{IH}$, the relative geometry of the MEA catheter, that is the relative location of all CIE and PME electrodes, is known. This may be accomplished by deploying the MEA catheter into a tightly controlled pre-declined shape. In this case the MEA catheter also needs to be designed such that it maintains its structure during cardiac contraction and while being maneuvered in the heart.

Equation 8 provides a forward relationship between $K_{CIE}$ the current $I_{CIE}$ (proportional to the current $I_{CIE}$), and surface voltage $V_S$, and the PME voltages $V_{PME}$. In the tracking problem $K_{CIE}$ and surface voltage $V_S$ are unknown while the PME voltages $V_{PME}$ are known. In some embodiments it may be assumed that $I_{CIE}$ and σ are a priori known, in which case $K_{CIE}$ is assumed to be known. The following describes a more general and preferred scenario where $K_{CIE}$ need not be known. An inverse relationship is employed to solve for $K_{CIE}$ and $V_S$. This inverse relationship may be posed as a least squares optimization problem:

$$\min_{V_S, K_{CIE}} \left( \| \hat{V}_{PME} - V_{PME} \|^2 + \alpha \cdot \| L \cdot \begin{bmatrix} V_S \\ K_{CIE} \end{bmatrix} \|^2 \right) \quad (9)$$

Where $V_{PME}$ are measured potentials, $\hat{V}_{PME}$ are computed expected potentials as defined in equation 8, α is a regularization parameter and L is a regularization operator. Examples of the use of inverse theory and regularization are described, for example, in patent application Ser. No. 11/451,898, entitled "NON-CONTACT CARDIAC MAPPING, INCLUDING MOVING CATHETER AND MULTI-BEAT INTEGRATION" and filed Jun. 13, 2006, the contents of which is incorporated by reference herein. In this case, since there is no need to regularize the current $I_{CIE}$, L is constructed such that $$L = \begin{bmatrix} & & & 0 \\ & L_s & & \vdots \\ & & & 0 \\ 0 & \cdots & 0 & 0 \end{bmatrix}.$$

Where $L_s$ is a regularization operator for the surface S. Tikhonov regularization may be used in this case. In the case of Tikhonov 0 regularization operator $L_s$ is the identity matrix, while in the case of Tikhonov 1 $L_s$ is the gradient operator on surface S. In experimentation, Tikhonov 1 has been found to outperform Tikhonov 0 and a regularization parameter α=0.1 has been found to be effective.

With $K_{CIE}$ and $V_S$ known, it is possible to compute the expected voltage measurement anywhere inside surface S.

Figure 13:
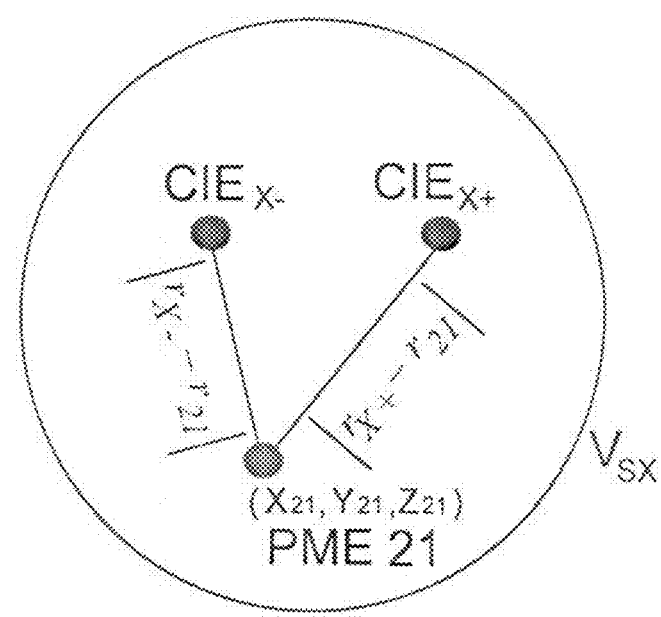
FIG. 13 is a schematic diagram of the distances between a source dipole electrode and the PME and a sink dipole electrode and the PME.

As shown in FIG. 13, if the tracked electrode (PME21) is inside the volume contained by surface S, its expected value can be computed as $$\hat{V}_{PME21,X} = \hat{V}_{DIP21,X} + V_{IH21,X} = A_{DIP,X}(\rho_{21}) \times K_{CIE,X} + A_{IH,X}(\rho_{21}) \times V_{z,X} \quad (10)$$

In this case, $\rho_{21} = (X_{21}, Y_{21}, Z_{21})$ is the location in 3D Cartesian coordinates for which the potential is being computed. Unlike equation 8 where the PME was assumed to be on the MEA, PME21 may be anywhere inside the volume contained by surface S. The computation of $\hat{V}_{PME21,X}$ is clone in a manner identical to equation 8, expect that it is done for a particular location $\rho_{21}$. In addition, the X subscript designates that the computation is done for the CIE pair along the X-axis.

The determination of the location of the PME is done in a similar manner to the method described above for the homogeneous case. The only difference being the computed results $(\hat{V}_{PME21,X}, \hat{V}_{PME21,Y}, \hat{V}_{PME21,Z})$ are obtained from the calibrated analysis rather than the homogeneous analysis. Equation (2) can be used in this case again and the same methods can be used for solving the optimization problem.

Figure 14A:
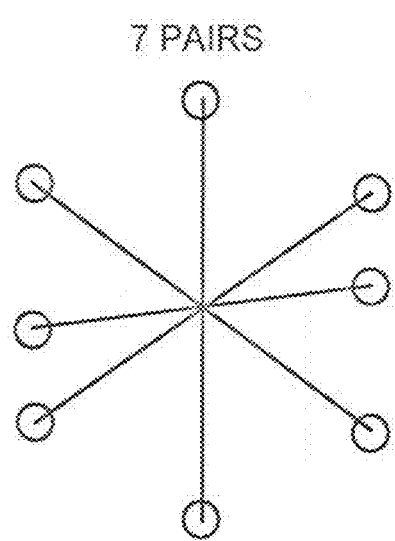
FIGS. 14A and 14B are schematic diagrams of two current injection electrodes (CIE) pair constellations.
Figure 14B:
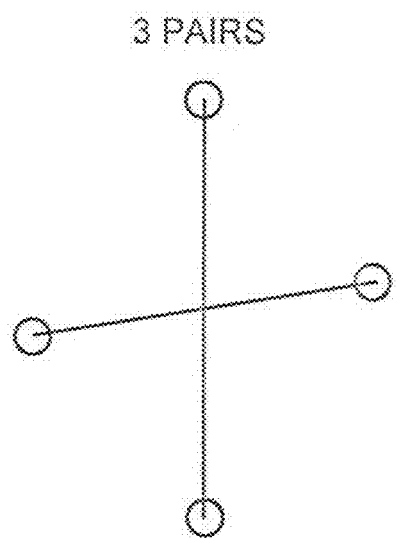

Configurations other than orthogonal pairs may be used for either method, and that more than 2 CIE may participate in current injection at a given time. FIGS. 14A and 14B show two different CIE pair constellations. FIG. 14B shows the 3 pair constellation described above while FIG. 14A hand side shows 7 pairs. The 7 pairs are the same 3, plus 4 additional diagonal pairs.

In the case of 7 pairs, the solution for p becomes overdetermined since we obtain 7 equations and 3 unknowns ((X,Y,Z) coordinates), which helps improve tracking accuracy depending on the specific embodiment.

Furthermore, more than one electrode (such as PME21) may be tracked simultaneously using either scheme. To do so, signals are acquired from and an optimization problem is solved for each of the electrodes being tracked. If such electrodes are mounted on different catheters then it is possible to simultaneously track multiple catheters.

As noted above, the measurements collected at the PMEs as a result of current injected by the CIE are generally affected by the complex conductivity, or admittivity, distribution of the medium. While the specific embodiment discussed above focus on the real part of the conductivity which affects the amplitude measured by the PMEs, additional information can also be obtained by accounting for the real part (conductivity) and imaginary part (permittivity) of the medium's complex conductivity, which affects the amplitude and phase of the signal measured by the PME. In this manner, the use of both amplitude and phase, or phase alone may also be used for tracking purposes. Use of the imaginary part of the complex conductivity is of particular importance in material distributions where the permittivity contrast exceeds that of the conductivity contrast.

To modify the mathematical formalism for the specific embodiments described above to account for imaginary part of the complex conductivity, the measurement expressed in Equation (1) is changed. Specifically, Equation (1) is modified as follows:

$$PME21, X^* = \frac{I_X^*}{4\pi\sigma_h^*}\left(\frac{1}{|r_{X+} - r_{21}|} - \frac{1}{|r_{X-} - r_{21}|}\right) \quad (11)$$

where $\sigma_h^*$ represents the complex conductivity defined as $\sigma^* = \sigma + i\omega\epsilon$, where $\sigma$ is the real component of conductivity, $\omega$ is the frequency of the current source, and $\epsilon$ is the electrical permittivity. The current and potential become complex as well, having both amplitude and phase. From Equation (11), one can obtain a corresponding optimization problem, analogous to Equation (2), that accounts for the complex conductivity, and determine location of tracked electrodes.

In a similar way complex conductivity can be accounted for in the inhomogeneous method by replacing $\sigma$ with $\sigma^*$ in any formula and replacing I and V with their complex representation. Similar numerical methods can be used for solving the complex Laplaces equation. KCIE, ICIE, VS and VPME take complex forms and Equation (9), the optimization problem for solving the inverse relationship, can also be solved for complex numbers. Once again, one can obtain a corresponding optimization problem, analogous to Equation (2), that accounts for the complex conductivity in the case of the calibrated analysis, and determine location of tracked electrodes.

The locations determined in the method described are all relative to the MEA catheter (e.g., catheter 1). It should be noted that both the MEA catheter itself and any of the tracked catheters and electrodes may be moving between measurements, and therefore the location is not determined with respect to any fixed coordinate system. A fixed coordinate system can be defined using any location that is fixed in space as an origin. If the origin is moving along with the organ in discussion then the coordinate system of the tracking system are relative to that organ, which can be advantageous if the organ itself is not fixed in space. In order to determine the location of the catheters with respect to the surface of the organ (e.g., the surface of the heart) in discussion some reference location data is used. Such fixed reference location can be provided using a tracked catheter in a fixed location in a way that will be explained below. It should be noted that an independent tracking system can be used for providing a fixed reference point and that this method will also be explained below.

Referring back to FIG. 5, in some embodiments catheter 2 is tracked relative to catheter 1. In another embodiment, more than one catheter may be tracked relative to catheter 1. When such relative locations are known, the location of any catheter relative to any other tracked catheter can be determined.

An independent tracking system may be used to track the location of one of the catheters as it is moved inside the cavity. Using this method the locations of all other tracked catheters can be determined as well. This provides a method of determining the locations of all catheters relative to the fixed coordinate system of the independent tracking system by having only one catheter directly tracked by that system.

An independent tracking system is a conventional tracking system based on tracking electric or magnetic signals generated externally and detected by one or more tracking elements, such as sensors, affixed to a catheter. Alternatively, tracking elements such as emitters or beacons affixed to the catheter may emit electric or magnetic signatures that are detected by an independent tracking system, and used to determine the location of the emitters, and thus the location and orientation of a catheter. For example, a collection of miniaturized coils oriented to detect orthogonal magnetic fields and forming a sensor can be placed inside the catheter to detect the generated magnetic fields. An independent tracking system is generally disposed outside the patient's body at a distance that enables the system to either generate radiation of suitable strength (i.e., generate signals whose amplitude will not harm the patient or otherwise interfere with the operation of other apparatus disposed in the near vicinity of the sensing and tracking system), or detect magnetic or electric radiation emitted by the emitters affixed to a catheter.

Keeping all tracked locations in the coordinate system of the cavity itself rather than in a fixed coordinate system results in a tracking system that compensates for movements of the cavity in space. Sources of such movements can be, for example, patient movements and patient respirations. If the effects of such movements are ignored error is introduced in the tracking process which exceeds the target accuracy requirements for some uses.

In some embodiments, as described in more detail herein, it is possible to reference the location data to the cavity without the use of an independent tracking system. For example, in the embodiment shown in FIG. 7, the tracking procedure is generally performed without the aid of an independent tracking system.

Referring back to FIG. 5, in some embodiments catheter 2 is tracked relative to catheter 1. In other embodiments catheter 2 may be positioned in a stable location (e.g. coronary sinus, atrial appendage, apex), and catheter 1 may be moved and tracked relative to catheter 2.

In some examples, more than one electrode may be positioned in a stable location and the position of MEA catheter 1 relative to the stable electrodes is determined. The addition of at least 3 stable electrodes that are somewhat distant (e.g. having a separation of greater than about 3 mm) from each other and assumed to be attached to a rigid body allows capturing cardiac rotation in addition to displacement. The arrangement of the reference electrodes in space can be referred to as a spatial distribution of points. The three reference electrodes are arranged to define a plane in space. For example, in order to determine 3-D movements of the organ, the electrodes are not placed on a straight line and it may be desirable for the electrodes to be somewhat distant from each other.

Figure 15:
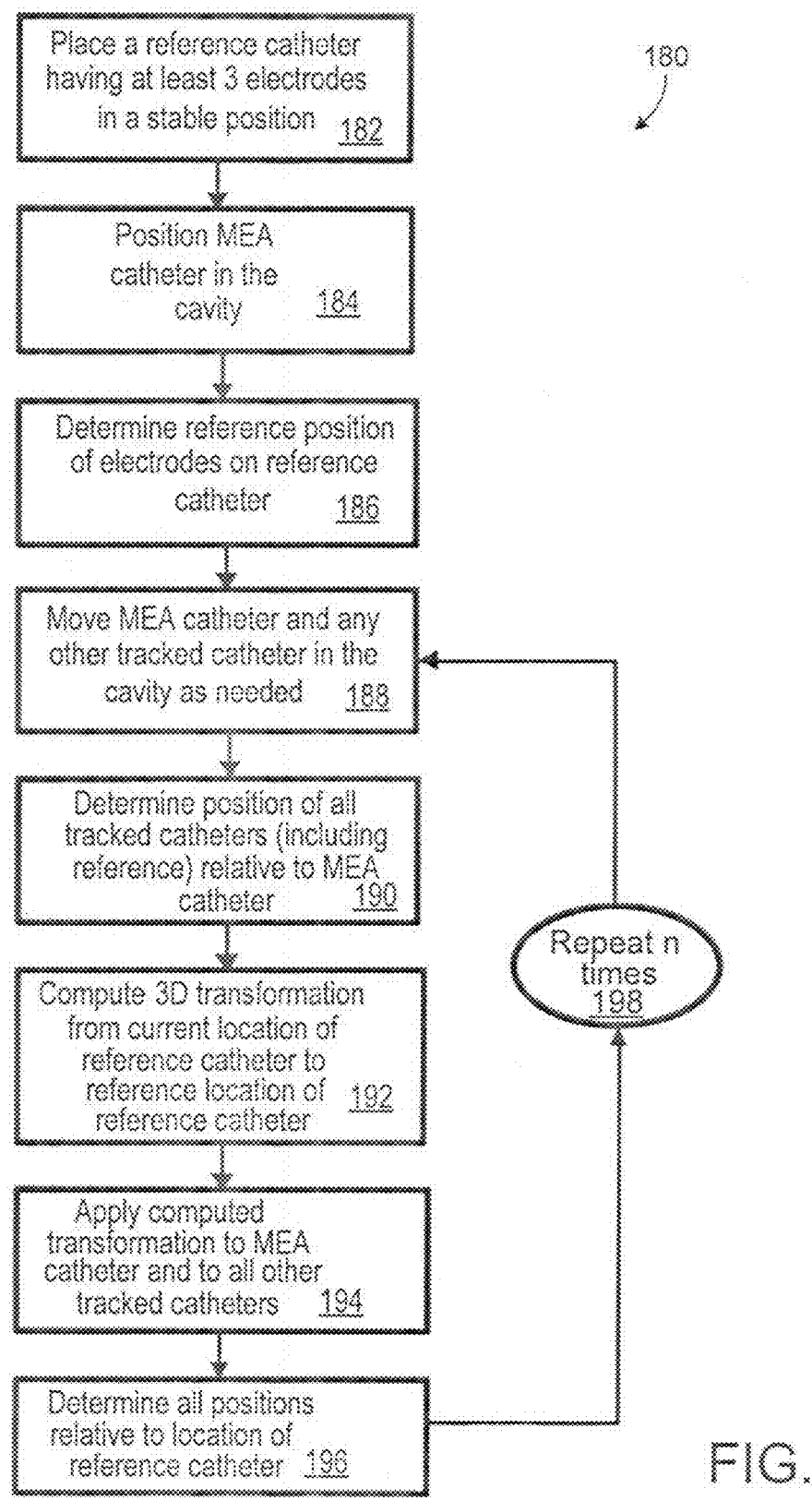
FIG. 15 is a flow diagram of an exemplary embodiment for determining the positions of electrodes relative to a surface of an organ.

FIG. 15 is a flow diagram providing a top-level depiction of a procedure 180 for determining positions of MEA catheter relative to the organ itself while accounting for the organ's movement. In this scenario several electrodes on catheter 2 can be tracked. In step 186, the catheter (including at least three electrodes) is secured in a stable position in the heart in a way that does not allow relative movement between the catheter and the heart walls. This can be done either by choosing a location such that the catheter will conform to the anatomy and will stay in a fixed position (e.g., coronary sinus or apex), or by using a fixation mechanism (e.g., fixation mechanisms such as the ones used for positioning pacing leads, anchoring mechanisms or a balloon mechanism). For convenience the electrodes secured in stable positions with respect to the surface of the organ can be referred to as reference electrodes and the catheter they are mounted on can be referred to as a reference catheter. It should be noted that in an embodiment where the reference catheter is located in the coronary sinus the tracked catheter is no longer inside the blood volume and the computational method explained is no longer completely accurate. However, the wall that separates the coronary sinus from the cardiac chamber is very thin, and analysis shows that the error introduced by this embodiment is small enough for the accuracy requirements of the system.

The positions of all the electrodes on catheter 2 are tracked for a period of several cardiac cycles. The locations are averaged over time period described and the average locations of the electrodes are considered the reference distribution of electrodes on catheter 2.

Since there is a movement of the catheter relative to the heart's surface during the cardiac cycle even if no external movement is introduced, it is necessary to gate the location measurement according to the cardiac cycle. In some example, this can be done by using electrical measurements of the cardiac cycle (e.g. by the use of surface ECG), triggering on a constant marker in the cardiac phase (e.g. using an R-wave detection algorithm, a threshold criterion, or a maximum criterion), dividing the cardiac cycle into m slices (e.g. m=10), and repeating the mentioned calculation for each slice separately. This method results in m reference electrode distributions for catheter 2, each one should be used as a reference in the appropriate phase of the heart cycle. In another example, the location measurement can be gated according to the cardiac cycle based signals measured by the PME. More particularly, cardiac contraction modulates the tracking signal detected by the PME on the MEA because the inhomogeneous component changes as the heart contracts. It is possible to detect this modulation of the signal and gate the location measurements to the cardiac cycle based on this detection in a similar way that an ECG signal is being used to gate the location measurements.

Once a reference distribution has been determined, any movement of the heart can be accounted for and all location measurements can be brought to the same coordinate system relative to the cavity. This is done by registering the location of catheter 2 at any given time to the location of the catheter in the reference measurement. More particularly, in step 184, the MEA catheter is positioned within the cavity and in step 186, the reference distribution of the reference electrodes on the reference catheter are determined. In step 188, the MEA catheter and/or other tracked catheters are moved in the cavity as needed. In step 190, the system determines the position of the tracked catheters (including the reference electrodes in the secured locations) relative to the MEA catheter. In step 192, the system computes a 3-dimensional transformation of the current location of the reference catheter to the previously computed reference position of the reference catheter. The registration transformation obtained in the process is, in step 194, applied to all tracked electrodes (and by that to all tracked catheters). In step 196, the positions of the electrodes relative to the location of the reference catheter are determined bringing the locations of each of the tracked electrodes to the same coordinate system relative to the cavity.

The registration transformation, $t_0$, is determined by minimizing the following expression:

$$\min_{t_a} \sum_{i=1}^{l} d_i^2 \qquad (12)$$

To perform the minimization of Equation (12), the vectors $R_{1\ldots l}$, representing the reference distribution (i.e. the locations of catheter 2 electrodes in the reference measurement), are defined. An exemplary value of l can be 3. Also defined are the vectors $P_{1\ldots l}$, which corresponds to the locations of catheter 2 electrodes in the current measurement, and the operator $T[t_0](P_i)$ which is a transformation operator performed on the points defined in vectors $P_i$. The resultant vector $t_0$ is represented as a six parameter transformation $[x_0, y_0, z_0, \theta_0, \phi_0, \psi_0,]$, where the first three parameters represent the translation and the last three represent the rotation.

The distance function D is defined such that $d_i=D(T[t_0](P_i), R_i)$ represents the distance from transformed point $T[t_0](P_i)$ to the respective reference electrode location $R_i$. To determine the vector to with respect to which the term $d_i$ for the current location measurement is minimized, a number of techniques may be used, including conventional iterative optimization techniques such as least-square error computation procedures and/or other mathematical regression and curve-fitting techniques.

After determining the transformation operator it can be applied to the measured location of catheter 1 to express this location in terms of the endocardium surface coordinate system, and in that manner transforms all other catheters tracked by catheter 1 to the same coordinate system.

The registration process is gated to the cardiac cycle in the same way the reference measurement was gated. Each registration vector $t_0$ is calculated using the reference locations $R_i$ measured at the same slice of the cardiac cycle as the tracking measurement that is being registered.

In some embodiments, the same method can be applied even if the reference electrodes are distributed between multiple catheters instead of being all on the same catheter. In one embodiment three separate catheters are positioned in stable locations and a single electrode is tracked on each one of them. The locations of the three tracked electrodes are then used for generating the reference distribution in the same manner described, and the rest of the registration method remains the same.

In some embodiments, the same method for registering a coordinate system of a tracking system to a cavity and compensating for movement of that cavity can be applied to other tracking systems. In one embodiment the three catheters that are tracked by an independent tracking system can be placed in stable positions and the locations of the tracked catheters can be used for generating the reference distribution in the same manner described. The reference distribution can be used in the same manner described for the registration method.

The registration method is not limited to a specific tracking system and is applicable to any system that can determine locations of multiple tracked objects. Keeping all tracked locations in the coordinate system of the cavity itself rather than the coordinate system of the tracking system results in a tracking system that compensates for movements of the cavity in space.

Mapping Procedure

The system can perform cardiac mapping (e.g., non-contact mapping) of electro-physiological information about the endocardium surface, as well as other operations. A description of the mapping and other procedures that may be performed are provided for example, in application Ser. No. 11/451,871, entitled "NON-CONTACT CARDIAC MAPPING, INCLUDING RESOLUTION MAP," and filed Jun. 13, 2006, the content of which is hereby incorporated by reference in its entirety, as well as application Ser. Nos. 11/451,898, and 11/451,908, referred to above.

Briefly, and with reference to FIG. 16, the catheter 110 may be moved to a first location within the heart chamber, at step 902, in which the first set of measurement by the catheter's multiple mapping electrodes is performed. Control of the catheter's movement and location within the heart chamber is performed manually by the operator manipulating the catheter 110. Alternatively, the movement of the catheter 110 within the heart chamber may be automated by use of techniques such as magnetic (see, e.g., Stereotaxis, Inc. of St. Louis, Mo.) or robotic (see, e.g., Hansen Robotics, Inc.) navigation. Catheter manipulation may be used to cause the catheter to follow a pre-determined displacement route to collect data at locations that may be considered to be of higher interest than others. For example, in some embodiments, the catheter 110 may be moved at specified displacement intervals in an area of the heart chamber that is known to have abnormal cardiac activity.

The 3D location of the catheter 110, and/or to its multiple electrodes, is then determined using one of the techniques discussed herein. A coordinate system transformation function between the frame of reference and the 3D representation of the heart cavity is applied to the coordinates of the catheter 110.

At its current location, the multiple mapping electrodes of the catheter 110 (which, as previously noted, may be the same as the PMEs used during the tracking process) acquire signals resulting from the heart's electrical activities (at 904).

The mapping system (which may be implemented using the same hardware used to implement system 100) generates reconstruction transformation functions, at step 906, to be applied on the acquired signals to reconstruct the electro-physiological information at the endocardium surface. The generated reconstruction transformation functions may be based, among other things, on pre-computed reconstruction transformation functions that were previously determined (generally prior to insertion of the catheter 110 into the patient's heart chamber), and the catheter's location relative to the endocardium surface. Thus, in some embodiments, for every location of the catheter 110 at which raw data is acquired, a corresponding set of reconstructed electro-physiological information is computed.

After the raw data corresponding to the heart's electrical activity has been acquired, recorded and processed using reconstruction transformation function(s) to obtain reconstructed electro-physiological information at the endocardium surface (also at step 906), a determination is made, at step 908, whether there are additional locations within the heart chamber to which the catheter 110 is to be moved. If there are additional locations in the heart chamber to which the catheter 110 needs to be moved the catheter is moved, using manual or automatic control, to the next location in the heart chamber, whereupon the operation described in relation to the steps 902-906 in FIG. 16 are performed for that next location.

To enhance the quality of the reconstructed electro-physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity).

In some embodiments, a composite set of electro-physiological information can be generated by selecting from multiple sets of reconstructed electro-physiological information portions of the reconstructed information. Selecting which portions of reconstructed information to use can be based on resolution maps that are indicative of the quality of the reconstructed information for a particular portion or set of the reconstructed electro-physiological information. Other criteria and techniques for selecting suitable portions of data to reconstruct a composite set of electro-physiological information may be used.

In some embodiments, one (or more) composite reconstruction transformation function is computed that is applied collectively to the raw data acquired at multiple locations to generate a resultant composite set of reconstructed electro-physiological information based on a substantial part of the data acquired. Such a transformation function represents a "mega transformation function" that corresponds to a "mega catheter," whose effective number of electrodes and electrode span is related to the number of locations to which the catheter was moved within the heart chamber. Under those circumstances the generation of the composite reconstruction transformation function is deferred until data is collected from the catheter's multiple locations.

Alternatively, in some embodiments, the "mega transformation function" and "mega catheter" may be updated on an ongoing basis to take into account a given relevant measurement window. This window may be a fixed number of measurements such that the arrival of new measurements displaces measurements that were obtained before the time window. This yields a constantly updating moving average.

In some embodiments, signals are measured throughout a heart beat cycle (for example, a measurement can be made at each catheter electrode at each of multiple, different phases of a single beat heart cycle).

Yet in further embodiments the reconstructed set of electro-physiological information is computed based on measurements taken over one or more heart beats. In the latter situation, the catheter is moved to a particular location, and acquires multiple sets of raw data over several heart beats. The acquired data is averaged, and the reconstruction process is applied to the averaged values. If the data is acquired over B heart beats (i.e., B measurements), an improvement in the signal-to-noise ratio proportional to $\sqrt{B}$ is obtained. The timing of the measurement operation is generally synchronized to ensure that measured data is acquired at approximately the same phase of the heart cycle.

If it is determined at 908 that there are no additional locations within the heart chamber at which data needs to be collected, then the non-contact mapping system may perform at 910 post-processing operations on the reconstructed electro-physiological information to extract clinically useful data. As noted, in some embodiments the mapping system produces a composite reconstructed set of electro-physiological information. Post processing operation are performed, under those circumstances, on the composite set of reconstructed electro-physiological information. In some circumstances where the non-contact mapping system produces multiple reconstructed sets of electro-physiological information for the raw data collected at each location in the heart chamber to which the catheter 110 was moved, the post processing operations are performed individually on one or more sets of reconstructed electro-physiological information.

In some embodiments, the post processing may involve nothing further then selecting a format for outputting (e.g., displaying) the reconstructed potentials to a user. In other embodiments, the post-processing may involve significant further mathematical manipulation of the reconstructed potentials to provide additional types of electro-physiological information.

The reconstructed electro-physiological information and/or sets of post-processed data are then displayed at 912. The information, be it the reconstructed electro-physiological information or any data resulting from the post-processing performed at 910, is displayed on a 3D graphical rendering of the 3D representation of the endocardium surface generated from the same data set acquired at 602 or at 502.

One of the post-processing operations performed on the reconstructed set(s) of electro-physiological information can include the generation of a resolution map. Such a resolution map indicates the spatial resolution of electro-physiological information at points on the endocardium surface, thereby providing a measure of the reliability and accuracy of the information at various points on the endocardium surface. The resolution map may also be used to form a composite set of reconstructed electro-physiological information by associating with individual sets of acquired raw data and/or individual sets of reconstructed electro-physiological information corresponding resolution maps. A resultant composite set is then formed by selecting portions of acquired raw data (or reconstructed information) whose reliability or accuracy, as indicated by the resolution map corresponding to the set from which the data is selected, is sufficiently high. Resolution maps may be used with any form of post-processing operation including all modes listed below. Strictly speaking, information about the resolution maps can be determined prior to obtaining the reconstructed potential data; however, herein we generally refer to the generation and display of the resolution map as "post-processing" because such information is typically presented to the user alter at least some of the potentials are reconstructed.

Another type of post-processing operation that may be performed includes the generation of isopotential maps. Particularly, where the reconstructed electro-physiological information pertains to electrical potentials, the reconstructed potentials may be color coded and superimposed on the 3D endocardial representation. Isopotential maps are the reconstructed potentials computed for every sampled time instance for a set of data acquired over a single or multiple heart beats.

Yet another type of post-processing operation includes the generation of timing maps (such as activation time maps). The timing maps provide information on the time-dependent behavior of the heart's electrical activity. Particularly, the activation map indicates at what point in time particular points on the endocardium surface experience a change in their electrical activity. For example, the activation map could identify the point in time at which particular cells on the endocardium surface experienced depolarization. Another type of timing map may be an iso-duration map where the amount of time certain tissue has been active for is detected. Timing maps may be computed from the reconstructed potentials over a single or multiple heart beats. Timing maps may be determined and displayed for one or more points on the endocardium surface representation.

Another type of post processing operation that may be performed at 910 is the generation of voltage maps. Voltage maps can be used to display characteristics of voltage amplitude in a given area. The voltage maps may be computed from the reconstructed potentials over a single or multiple heart beats. Useful voltage map information that may be determined and displayed for one or more points on the endocardium surface representation includes the maximum amplitude, or root mean square potential values.

Another type of post-processing operation is the generation of a difference map. The difference map provides information regarding the effectiveness of the clinical procedure (e.g., ablation) performed on the patient to ameliorate the symptoms of arrhythmias. The difference map compares the electrical behavior of the heart, as reflected from two or more voltage maps generated before and after the performance of the particular clinical procedure.

A further type of post processing operation is the generation of frequency maps. Frequency mapping, and more generally spectral analysis, are used to identify on the endocardium surface localized sites of high-frequency activity during fibrillation. Frequency maps are computed by acquiring multiple sets of reconstructed information over a particular time interval which includes a single or multiple heart beats. The acquired raw data is then used to obtain the frequency representation of that data. Specific information (e.g., dominant frequency components) from the frequency representation is subsequently identified, and that identified information may be displayed.

Other types of post-processing information may likewise be performed at 910.

Other Embodiments

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

A number of embodiments of the invention have been described. Nevertheless, it will be understood that various modifications may be made without departing from the spirit and scope of the invention. For example, as noted above, while the discussion above focused on the automatic registration of the coordinate system of a representation of the heart to the coordinate system of an object inserted into the medium enclosed within the heart (namely, the intracardiac blood), the procedures and systems described herein may also be adapted to be used for registering the coordinate system of representations of other objects that can be characterized as a distribution of materials having different conductivities.

Furthermore, while it is generally preferred that complete information about the position of the object is determined, such as the location of a point of the object and the orientation of the object with respect to that point; in other embodiments, the determined position for the object may include fewer than all of these degrees of freedom.

Accordingly, other embodiments are within the scope of the following claims.

What is claimed is:

1. A method comprising:
   causing, current to flow between each of three or more sets of current-injecting electrodes on a first catheter inserted into an organ in a patient's body, the organ having a periphery;
   in response to current flow caused by each set of current injecting electrodes, measuring an electrical signal at each of one or more measuring electrodes located on one or more additional catheters inserted into the organ in the patient's body; and
   determining a position of each of one or more of the measuring electrodes on the one or more additional catheters relative to the current-injecting electrodes on the first catheter based on the measured signals from the one or more measuring electrodes.

2. The method of claim 1, further comprising measuring electric signals at each of multiple measuring electrodes on the first catheter in response to current flow caused by each set of current injecting electrodes, and wherein the determination of the relative position between the first catheter and each of the one or more of the measuring electrodes on the one or more additional catheters is based on the measured signals for the measuring electrodes on the first catheter and the one or more additional catheters.

3. The method of claim 2, wherein the determination associates each measured signal with a homogeneous component that depends on the relative position of each signal measuring electrode with respect to each set of current injecting electrodes and an inhomogeneous component associated with the periphery of the organ, the inhomogeneous component being modeled as a variation in electric potential along a surface enclosing at least the first catheter that depends on the relative positions between the current injecting electrodes and the signal measuring electrodes.

4. The method of claim 3, wherein the homogeneous component further depends on an estimate for conductivity inside the organ.

5. The method of claim 2, wherein the determination accounts for a change in conductivity at the organ's periphery.

6. The method of claim 2, wherein the organ comprises the patient's heart and the determination accounts for a change in conductivity at the cardiac chamber periphery.

7. The method of claim 2, wherein the determination associates each measured signal with a homogeneous component and an inhomogeneous component associated with the organ's periphery.

8. The method of claim 2, wherein the first catheter comprises more than 32 measuring electrodes.

9. The method of claim 2, wherein the determination is based on predetermined information about the relative positions of the electrodes on the first catheter.

10. The method of claim 2, wherein the determination comprises an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter and the change in conductivity at the organ's periphery.

11. The method of claim 2, wherein the determination comprises an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter and the estimate for conductivity inside the organ.

12. The method of claim 2, wherein the determination comprises an optimization technique that minimizes collective differences between each of the measured signals and an estimate for each of the respective measured signals as a function of the relative position between each of the measuring electrodes on the first and the one or more additional catheters and the sets of current-injecting electrodes on the first catheter, the change in conductivity at the organ's periphery and the estimate for conductivity inside the organ.

13. The method of claim 2, further comprising using the multiple signal measuring electrodes on the first catheter to measure cardiac signals.

14. The method of claim 1, further comprising securing at least three electrodes to be used for reference to fixed locations within the organ.

15. The method of claim 14, wherein the electrodes used for reference comprise measuring electrodes and the method further comprises determining the position of each of the electrodes used for reference relative to the first catheter.

16. The method of claim 14, wherein the at least three electrodes used for reference are on a single catheter.

17. The method of claim 16, further comprising using the determined position of each of the reference electrodes relative to the first catheter to determine a location of each of the one or more electrodes on the one of more additional catheters relative to the surface of the organ.

18. The method of claim 17, further comprising displaying the position of the one or more additional catheters relative to the surface of the organ.

19. The method of claim 16, further comprising using the determined position of each of the reference electrodes relative to the first catheter to determine a location of the first catheter relative to the surface of the organ.

20. The method of claim 19, further comprising displaying the position of the first catheter relative to the surface of the organ.

21. The method of claim 14, further comprising determining a position of each of the reference electrodes relative to the first catheter and determining a location of each of the one or more electrodes on the one or more additional catheters relative to the surface of the organ.

22. The method of claim 21, wherein determining a location of each of the one or more electrodes on the one or more additional catheters relative to the surface of the organ comprises correcting a location of the one or more additional catheters based on a movement of the organ.

23. The method of claim 22, wherein the movement of the organ comprises a translation of the organ.

24. The method of claim 22, wherein the movement of the organ comprises a rotation of the organ.

25. The method of claim 22, wherein the movement of the organ comprises a movement caused by respiration.

26. The method of claim 22, wherein the movement of the organ comprises a movement caused by movement of the patient.

27. The method of claim 21, wherein determining a location of each of the one or more electrodes on the second catheter relative to the surface of the organ comprises correcting a location of each of the one or more electrodes on the second catheter based on a movement of the first catheter.

28. The method of claim 14, further comprising using the reference electrodes to generate a fixed coordinate system relative to a surface of the organ.

29. The method of claim 14, further comprising determining the position of each of the one or more measuring electrodes on the second catheter relative to the surface of the organ.

30. The method of claim 14, further comprising determining the position of each of the one or more the measuring electrodes on the second catheter relative to the surface of the organ by solving an optimization problem that minimizes collective difference between a reference distribution of the reference electrodes based on the fixed locations and a determined position of each of the reference electrodes.

31. The method of claim 14, further comprising moving the first catheter within the organ relative to the reference electrodes.

32. The method of claim 31, further comprising tracking the position of the first catheter relative to the surface of the organ based on the measured signals on the first catheter and the fixed location of the reference electrodes.

33. The method of claim 1, further comprising using multiple signal measuring electrodes on the first catheter and the one or more electrodes on the one or more additional catheters to measure cardiac signals.

34. The method of claim 1, further comprising using the same one or more measuring electrodes on the one or more additional catheters to measure the electrical signals to determine the position of the one or more electrodes and to measure cardiac signals.

35. The method of claim 1, further comprising using one or more electrodes on the one or more additional catheters for delivering ablation energy for ablating tissue of the organ.

36. The method of claim 1, further comprising moving one or more of the additional catheters inside the organ and tracking the position of each of one or more measuring electrodes relative to the surface of the organ based on signals measured by the one or more measuring electrodes in response to current flow caused by each set of current injecting electrodes on the first catheter and the tracked position of the first catheter relative to the surface of the organ.

37. The method of claim 1, further comprising using a catheter to ablate selected regions of the organ based on the measured electrical activity and a tracked position of an electrode on the catheter used to ablate the selected regions.

38. The method of claim 37, further comprising moving a catheter comprising an ablation electrode inside the organ and tracking the position of the ablation electrode on that catheter relative to the surface of the organ based on signals measured by the ablation electrode in response to current flow caused by each set of current injecting electrodes on the first catheter.

39. The method of claim 38, further comprising using the ablation electrode on the catheter to ablate selected regions of a cardiac chamber.

40. The method of claim 1, wherein the one or more additional catheters comprises at least two additional catheters.

41. The method of claim 1, wherein measuring the electrical signal at each of the one or more measuring electrodes on the one or more additional catheters comprises simultaneously measuring the electrical signal at each the one or more measuring electrodes on the one or more additional catheters.

42. The method of claim 1, wherein three or more sets of current-injecting electrodes on a first catheter comprise three or more pairs of current-injecting electrodes configured to generate a dipole potential.

43. The method of claim 1, wherein three or more sets of current-injecting electrodes on a first catheter comprise three or more sets of current-injecting electrodes configured to generate a quadropole potential.

44. The method of claim 1, wherein the determination comprises an optimization technique that minimizes collective differences between each of the measured signals and an estimate for each of the respective measured signals as a function of the relative position between each of the one or more measuring electrodes on the one or more additional catheters and the sets of current-injecting electrodes on the first catheter.

45. The method of claim 1, wherein causing the current to flow between each of the three or more sets of current-injecting electrodes on the first catheter comprises modulating the current caused to flow between each of the three or more sets of current-injecting electrodes in frequency.

46. The method of claim 1, wherein determining the position of each of the one or more measuring electrodes on the one or more additional catheters relative to the first catheter based on the measured signals from the one or more electrodes comprises distinguishing the current from a particular one of the three or more sets of current-injecting electrodes from other electrical signals.

47. The method of claim 46, wherein the other electrical signals comprise currents from other ones of the three or more sets of current injecting electrodes.

48. The method of claim 46, wherein the other electrical signals comprise a cardiac signal.

49. The method of claim 1, wherein the current is caused to flow at a frequency outside the frequency range of the patient's cardiac activity.

50. The method of claim 1, wherein determining the position of each of the one or more measuring electrodes on the second catheter relative to the first catheter based on the measured signals from the one or more electrodes comprises distinguishing cardiac signals from signals responsive to the injected current.

51. The method of claim 50, wherein distinguishing cardiac signals from signals responsive to the injected current comprises using a spread spectrum technique.

52. The method of claim 1, wherein the determination of the relative position between the first catheter and the one or more electrodes on the one or more additional catheters is repeated multiple times during the patient's cardiac cycle.

53. The method of claim 1, wherein the first catheter comprises three or more pairs of current-injecting electrodes.

54. The method of claim 1, wherein three of the current injecting electrode sets define substantially orthogonal axes.

55. The method of claim 1, wherein causing current to flow between each of three or more sets of current injecting electrodes comprises sequentially causing current to flow between each of three or more sets of current injecting electrodes.

56. The method of claim 1, wherein causing current to flow between each of three or more sets of current injecting electrodes comprises concurrently causing current to flow between multiple sets of the three or more sets of current injecting electrodes, wherein the frequency of the current differs between the sets of current injecting electrodes.

57. The method of claim 1, wherein causing current to flow between each of three or more sets of current injecting electrodes comprises modulating each current with information for coding division of the currents from the three or more sets of current injecting electrodes.

58. The method of claim 1, wherein causing current to flow between each of three or more sets of current injecting electrodes comprises causing current to flow between each of three or more pairs of current injecting electrodes.

59. The method of claim 1, wherein the organ in the patient's body comprises the patient's heart.

60. The method of claim 1, further comprising using the determined position of each of the one or more electrodes on the one or more additional catheters to determine a position of the one or more additional catheters or portion of one or more of the catheters.

61. The method of claim 1, further comprising using the determined position of each of the one or more electrodes on the one or more additional catheters to determine a position of a portion of a catheter used for ablation.

62. The method of claim 1, further comprising displaying the position of the one or more additional catheters relative to a surface of the organ.

63. The method of claim 1, wherein the determination of the position of each of the one or more measuring electrodes on the one or more additional catheters relative to the first catheter accounts for a change in conductivity at the organ's periphery.

64. The method of claim 1, wherein the organ comprises the patient's heart and the determination accounts for a change in conductivity at a periphery of the cardiac chamber.

65. The method of claim 1, wherein the determination associates each measured signal with a homogeneous component and an inhomogeneous component associated with the organ's periphery.

66. The method of claim 65, wherein the inhomogeneous component is modeled as a variation in electric potential along a surface enclosing the first and second catheters that depends on the relative positions between the current injecting electrodes and each of the one or more measuring electrodes.

67. The method of claim 66, wherein the inhomogeneous component further depends on a regularization parameter.

68. The method of claim 65, wherein the homogeneous component corresponds to a dipole potential in a medium with a homogeneous conductivity.

69. The method of claim 65, wherein the homogeneous component corresponds to a quadropole potential in a medium with a homogeneous conductivity.

70. The method of claim 65, wherein the homogeneous component depends on the relative position of each signal measuring electrode with respect to each set of current injecting electrodes.

71. The method of claim 65, wherein the homogeneous component further depends on an estimate for conductivity inside the organ.

72. The method of claim 71, wherein the determination comprises an optimization technique that minimizes collective differences between each of the measured signals and an estimate for each of the respective measured signals as a function of the relative position between the one or more measuring electrodes on the one or more additional catheters and the first catheter and the estimated conductivity.

73. A system comprising:
a first catheter configured for insertion into an organ in a patient's body and comprising three or more sets of current injecting electrodes;
one or more additional catheters configured for insertion into the organ in the patient's body and comprising one or more measuring electrodes;
an electronic control system coupled to the first catheter and the one or more additional catheters and configured to cause current to flow between each set of current-injecting electrodes and measure an electrical signal in response to the current flow caused by each set of current injecting electrodes at each of the measuring electrodes on the one or more additional catheters; and
a processing system coupled to the electronic system and configured to determine the position of the each of one or more of the one or more current measuring electrodes relative to the current-injection electrodes of the first catheter based on the measured signals from the one or more measuring electrodes.

74. A system comprising:
a processing system configured for use with:
a first catheter configured for insertion into an organ in a patient's body and comprising three or more sets of current injecting electrodes;
one or more additional catheters configured for insertion into the organ in the patient's body and comprising one or more measuring electrodes; and
an electronic control system coupled to the first catheter and the one or more additional catheters and configured to cause current to flow between each set of current-injecting electrodes and measure an electrical signal in response to the current flow caused by each set of current injecting electrodes at each of the measuring electrodes on the one or more additional catheters,
where in the processing system is configured to be coupled to the electronic system and configured to determine a position of the each of one or more of the one or more current measuring electrodes relative to the current-injecting electrodes on the first catheter based on the measured signals from the one or more measuring electrodes.

75. The system of claim 74 further comprising one or more of: the first catheter; the one or more additional catheters; and the electronic control system.

76. A non-transitory computer program product residing on a computer readable medium, the computer program product comprising instructions for causing a computer to:
cause current to flow between each of three or more sets of current-injecting electrodes on a first catheter inserted into an organ in a patient's body, the organ having a periphery;
in response to current flow caused by each set of current injecting electrodes, measure an electrical signal at each of one or more measuring electrodes located on one or more additional catheters inserted into the organ in the patient's body; and
determine a position of each of one or more or the measuring electrodes on the additional catheters relative to the current-injecting electrodes on the first catheter based on the measured signals from the one or more measuring electrodes.

77. A non-transitory computer program product residing on a computer readable medium, the computer program product comprising instructions for causing a computer to:
cause current to flow between each set of at least three sets of current-injecting electrodes on a first catheter;
receive data relating to a measurement of an electrical signal measured in response to the current flow caused by each set of current injecting electrodes at each of the measuring electrodes on the one or more additional catheters, and
determine a position of the each of one or more of the one or more current measuring electrodes relative to the current-injecting electrodes on the first catheter based on the measured signals from the one or more measuring electrodes.

* * * * *

UNITED STATES PATENT AND TRADEMARK OFFICE
CERTIFICATE OF CORRECTION

PATENT NO. : 8,463,368 B2
APPLICATION NO. : 13/466511
DATED : June 11, 2013
INVENTOR(S) : Doron Harlev, Rotem Eldar and Zsolt Badics It is certified that error appears in the above-identified patent and that said Letters Patent is hereby corrected as shown below:

Title Page 2, Col. 2 Item 56 (Other Publications), Line 16, Delete "Ma Nagement" and insert
-- Management --

Title Page 2, Col. 2 Item 56 (Other Publications), Line 16, Delete "Arrhytmias" and insert
-- Arrhythmias --

Title Page 2, Col. 2 Item 56 (Other Publications), Line 38, Delete "Isoalted" and insert
-- Isolated --

Title Page 3, Col. 1 Item 56 (Other Publications), Line 17, Delete "Cateter" and insert
-- Catheter --

Title Page 3, Col. 1 Item 56 (Other Publications), Line 26, Delete "Contruction" and insert
-- Construction --

Title Page 3, Col. 1 Item 56 (Other Publications), Line 34, Delete "Appraoch" and insert
-- Approach --

Title Page 3, Col. 1 Item 56 (Other Publications), Line 67, Delete "Comptational" and insert
-- Computational --

Title Page 3, Col. 1 Item 56 (Other Publications), Line 72, Delete "Echcardiography" and insert
-- Echocardiography --

Title Page 3, Col. 2 Item 56 (Other Publications), Line 1, Delete "Intramyocarial" and insert
-- Intramyocardial --

Title Page 3, Col. 2 Item 56 (Other Publications), Line 13, Delete "Obained" and insert
-- Obtained --

Signed and Sealed this
Twentieth Day of August, 2013

Teresa Stanek Rea
*Acting Director of the United States Patent and Trademark Office*

CERTIFICATE OF CORRECTION (continued)
U.S. Pat. No. 8,463,368 B2

Title Page 3, Col. 2 Item 56 (Other Publications), Line 48, Delete "Matematics" and insert -- Mathematics --

Title Page 3, Col. 2 Item 56 (Other Publications), Line 68, Delete "Ventrical" and insert -- Ventricle --

Title Page 4, Col. 2 Item 56 (Other Publications), Line 3, Delete "exitable" and insert -- excitable --

In the Claims

Col. 36, Line 21, In Claim 1, delete "causing," and insert -- causing --

Col. 39, Line 20, In Claim 43, delete "quadropole" and insert -- quadruple --

Col. 40, Line 57, In Claim 69, delete "quadropole" and insert -- quadruple --

Col. 42, Line 22, In Claim 76, delete "or the" and inset -- of the --